(12) United States Patent
Fisher

(10) Patent No.: US 10,098,628 B2
(45) Date of Patent: Oct. 16, 2018

(54) ANCHOR DEPLOYMENT SYSTEM, DEVICE, AND METHOD OF TREATMENT

(71) Applicant: Cook Medical Technologies LLC, Bloomington, IN (US)

(72) Inventor: Benjamin Fisher, Martinsville, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 350 days.

(21) Appl. No.: 14/798,946

(22) Filed: Jul. 14, 2015

(65) Prior Publication Data

US 2016/0022259 A1 Jan. 28, 2016

Related U.S. Application Data

(60) Provisional application No. 62/027,328, filed on Jul. 22, 2014.

(51) Int. Cl.
*A61B 17/04* (2006.01)
*A61B 17/00* (2006.01)
(Continued)

(52) U.S. Cl.
CPC ...... *A61B 17/0401* (2013.01); *A61B 17/0483* (2013.01); *A61B 2017/00367* (2013.01); *A61B 2017/00818* (2013.01); *A61B 2017/0409* (2013.01); *A61B 2017/0417* (2013.01); *A61B 2017/0448* (2013.01); *A61B 2017/0464* (2013.01); *A61B 2017/061* (2013.01); *A61B 2090/395* (2016.02)

(58) Field of Classification Search
CPC ........ A61B 2017/0448; A61B 17/0483; A61B 2017/0417; A61B 2017/00367; A61B 2017/00818; A61B 2017/0409; A61B 17/0401

See application file for complete search history.

(56) References Cited

U.S. PATENT DOCUMENTS 1,673,486 A 6/1928 Berge
2,075,508 A 3/1937 Davidson
(Continued)

FOREIGN PATENT DOCUMENTS

EP 1159919 5/2001
EP 0831743 7/2003
(Continued)

OTHER PUBLICATIONS

Cook Incorporated "Cope Gastrointestinal Suture Anchor Sets," Cookmedical.com, pp. 1-44, 2012.

*Primary Examiner* — Richard Louis
(74) *Attorney, Agent, or Firm* — Buchanan Van Tuinen LLC

(57) ABSTRACT

Anchor deployment systems, anchor deployment devices, and methods of treatment are described herein. An embodiment of an anchor deployment system comprises a deployment device, a retention mechanism, an anchor, and a connector. The deployment device has a handle, an elongate member, a stylet, a spring, and an actuator. The deployment device has a first configuration in which the connector is releasably attached to the handle and a second configuration in which the connector is free of attachment to the handle.

15 Claims, 7 Drawing Sheets

(51) Int. Cl.
*A61B 17/06* (2006.01)
*A61B 90/00* (2016.01)

(56) References Cited

U.S. PATENT DOCUMENTS

| | | | |
|---|---|---|---|
| 2,579,192 A | 8/1950 | Kohl | |
| 3,664,345 A | 5/1972 | Dabbs et al. | |
| 4,235,238 A | 11/1980 | Ogui et al. | |
| 4,249,535 A | 2/1981 | Hargest, III | |
| 4,291,698 A | 9/1981 | Fuchs et al. | |
| 4,315,513 A | 2/1982 | Nawash et al. | |
| 4,393,873 A | 7/1983 | Nawash et al. | |
| 4,666,433 A | 5/1987 | Parks | |
| 4,685,901 A | 8/1987 | Parks | |
| 4,701,163 A | 10/1987 | Parks | |
| 4,705,040 A | 11/1987 | Mueller et al. | |
| 4,798,592 A | 1/1989 | Parks | |
| 4,823,794 A | 4/1989 | Pierce | |
| 4,852,568 A | 8/1989 | Kensey | |
| 4,890,612 A | 1/1990 | Kensey | |
| 5,019,093 A | 5/1991 | Kaplan et al. | |
| 5,037,429 A | 8/1991 | Hermes et al. | |
| 5,041,129 A | 8/1991 | Hayhurst et al. | |
| 5,049,138 A | 9/1991 | Chevalier et al. | |
| 5,051,272 A | 9/1991 | Hermes et al. | |
| 5,053,047 A | 10/1991 | Yoon | |
| 5,061,274 A | 10/1991 | Kensey | |
| 5,074,846 A | 12/1991 | Clegg et al. | |
| 5,112,310 A | 5/1992 | Grobe | |
| 5,121,836 A | 6/1992 | Brown et al. | |
| 5,123,912 A | 6/1992 | Kaplan et al. | |
| 5,123,914 A | 6/1992 | Cope | |
| 5,129,511 A | 7/1992 | Brown et al. | |
| RE34,021 E | 8/1992 | Mueller et al. | |
| 5,154,283 A | 10/1992 | Brown | |
| 5,172,702 A | 10/1992 | Leigh et al. | |
| 5,161,542 A | 11/1992 | Palestrant | |
| 5,167,627 A | 12/1992 | Clegg et al. | |
| 5,192,302 A | 3/1993 | Kensey et al. | |
| 5,222,976 A | 6/1993 | Yoon | |
| 5,222,978 A | 6/1993 | Kaplan et al. | |
| 5,226,912 A | 7/1993 | Kaplan et al. | |
| 5,246,104 A | 9/1993 | Brown et al. | |
| 5,249,582 A | 10/1993 | Taylor | |
| 5,258,015 A | 11/1993 | Li et al. | |
| 5,261,210 A | 11/1993 | Brown | |
| 5,261,886 A | 11/1993 | Chesterfield et al. | |
| 5,269,809 A | 12/1993 | Hayhurst et al. | |
| 5,273,529 A | 12/1993 | Idowu | |
| 5,306,289 A | 4/1994 | Kaplan et al. | |
| 5,307,924 A | 5/1994 | Manosalva et al. | |
| 5,312,345 A | 5/1994 | Cole | |
| 5,312,435 A | 5/1994 | Nash et al. | |
| 5,316,013 A | 5/1994 | Striebel et al. | |
| 5,318,543 A | 6/1994 | Ross et al. | |
| 5,330,503 A | 7/1994 | Yoon | |
| 5,341,823 A | 8/1994 | Manosalva | |
| 5,359,831 A | 11/1994 | Brown et al. | |
| 5,366,081 A | 11/1994 | Kaplan et al. | |
| RE34,866 E | 2/1995 | Kensey et al. | |
| 5,391,159 A | 2/1995 | Hirsch et al. | |
| 5,417,036 A | 5/1995 | Brown | |
| 5,425,445 A | 6/1995 | Brown et al. | |
| 5,447,966 A | 9/1995 | Hermes et al. | |
| 5,451,212 A | 9/1995 | Andersen | |
| 5,456,697 A | 10/1995 | Chesterfield et al. | |
| 5,462,162 A | 10/1995 | Kaplan et al. | |
| 5,468,252 A | 11/1995 | Kaplan et al. | |
| 5,480,405 A | 1/1996 | Yoon | |
| 5,531,699 A | 7/1996 | Tomba et al. | |
| 5,531,759 A | 7/1996 | Kensey et al. | |
| 5,531,761 A | 7/1996 | Yoon | |
| 5,538,010 A | 7/1996 | Darr et al. | |
| 5,545,178 A | 8/1996 | Kensey et al. | |
| 5,626,614 A | 5/1997 | Hart | |
| 5,702,352 A | 12/1997 | Kimura et al. | |
| 5,743,882 A | 4/1998 | Luther | |
| 5,779,647 A | 7/1998 | Chau et al. | |
| 5,830,231 A | 11/1998 | Geiges, Jr. | |
| 5,849,019 A | 12/1998 | Yoon | |
| 5,851,195 A | 12/1998 | Gill | |
| 5,944,739 A | 8/1999 | Zlock et al. | |
| 6,039,714 A | 3/2000 | Cracauer et al. | |
| 6,063,106 A | 5/2000 | Gibson | |
| 6,077,250 A | 6/2000 | Snow et al. | |
| 6,090,073 A | 7/2000 | Gill | |
| 6,106,499 A | 8/2000 | Overton et al. | |
| 6,110,183 A | 8/2000 | Cope | |
| 6,030,364 A | 12/2000 | Durgin et al. | |
| 6,186,985 B1 | 2/2001 | Snow | |
| 6,217,591 B1 | 4/2001 | Egan et al. | |
| 6,260,699 B1 | 7/2001 | Kaplan et al. | |
| 6,293,961 B2 | 9/2001 | Schwartz et al. | |
| 6,315,789 B1 | 11/2001 | Cragg | |
| 6,319,271 B1 | 11/2001 | Schwartz et al. | |
| 6,328,720 B1 | 12/2001 | McNally et al. | |
| 6,332,877 B1 | 12/2001 | Michels | |
| 6,402,722 B1 | 6/2002 | Snow et al. | |
| 6,432,123 B2 | 8/2002 | Schwartz et al. | |
| 6,582,443 B2 | 6/2003 | Cabak et al. | |
| 6,626,919 B1 | 9/2003 | Swanstrom | |
| 6,629,957 B1 | 10/2003 | Wiklund | |
| 6,673,058 B2 | 1/2004 | Snow | |
| 6,699,263 B2 | 3/2004 | Cope | |
| 6,773,440 B2 | 8/2004 | Gannoe et al. | |
| 6,896,665 B2 | 5/2005 | Picha et al. | |
| 6,902,541 B2 | 6/2005 | McNally et al. | |
| 6,966,916 B2 | 11/2005 | Kumar | |
| 6,997,931 B2 | 2/2006 | Sauer et al. | |
| 7,033,380 B2 | 4/2006 | Schwartz et al. | |
| 7,066,944 B2 | 6/2006 | Laufer et al. | |
| 7,416,554 B2 | 8/2008 | Lam et al. | |
| 7,534,248 B2 | 5/2009 | Mikkaichi et al. | |
| 7,582,098 B2 | 9/2009 | Gobel | |
| 7,815,659 B2 | 10/2010 | Conlon et al. | |
| 7,815,662 B2 | 10/2010 | Spivey et al. | |
| 7,867,253 B2 | 1/2011 | McMichael et al. | |
| 7,879,051 B2 | 2/2011 | Swain et al. | |
| 8,109,943 B2 | 2/2012 | Boraiah et al. | |
| 8,157,816 B2 | 4/2012 | Rotella et al. | |
| 8,333,776 B2 | 12/2012 | Cheng et al. | |
| 8,382,772 B2 | 2/2013 | Rotella et al. | |
| 8,480,986 B2 | 7/2013 | Bakos et al. | |
| 8,490,713 B2 | 7/2013 | Furnish et al. | |
| 8,545,521 B2 | 10/2013 | McClurg et al. | |
| 8,579,921 B2 | 11/2013 | Hathaway et al. | |
| 8,845,710 B2 | 9/2014 | Hendriksen et al. | |
| 2004/0034369 A1 | 2/2004 | Sauer et al. | |
| 2004/0153103 A1 | 8/2004 | Schwartz et al. | |
| 2004/0226145 A1 | 11/2004 | Ouellette et al. | |
| 2004/0267209 A1 | 12/2004 | Kunishige | |
| 2005/0004540 A1 | 1/2005 | McNally et al. | |
| 2005/0020988 A1 | 1/2005 | Woehr et al. | |
| 2005/0143691 A1 | 6/2005 | Picha et al. | |
| 2005/0149120 A1 | 7/2005 | Collier et al. | |
| 2005/0149121 A1 | 7/2005 | Crombie et al. | |
| 2005/0165419 A1 | 7/2005 | Sauer et al. | |
| 2005/0203550 A1 | 9/2005 | Laufer et al. | |
| 2006/0095008 A1 | 5/2006 | Lampropoulos | |
| 2006/0100643 A1 | 5/2006 | Laufer et al. | |
| 2006/0135991 A1* | 6/2006 | Kawaura | A61B 17/0057 606/213 |
| 2006/0135996 A1 | 6/2006 | Schwartz et al. | |
| 2009/0062742 A1 | 3/2009 | Rotells et al. | |
| 2009/0062743 A1 | 3/2009 | Rotells et al. | |
| 2013/0096582 A1 | 4/2013 | Cheng et al. | |
| 2013/0116710 A1 | 5/2013 | Ziniti et al. | |
| 2013/0165953 A1 | 6/2013 | Oba et al. | |
| 2013/0218206 A1 | 8/2013 | Gadlage | |

(56) References Cited

U.S. PATENT DOCUMENTS

2013/0226237 A1 8/2013 Stanley et al.
2013/0238024 A1 9/2013 Taylor et al.

FOREIGN PATENT DOCUMENTS

| EP | 1749481 | 2/2007 |
|---|---|---|
| EP | 1884199 A1 | 2/2008 |
| EP | 1884198 B1 | 3/2010 |
| WO | WO1995003837 | 2/1995 |
| WO | WO1998026821 | 12/1997 |
| WO | WO2002066108 | 8/2002 |
| WO | WO2006111394 | 10/2006 |

* cited by examiner

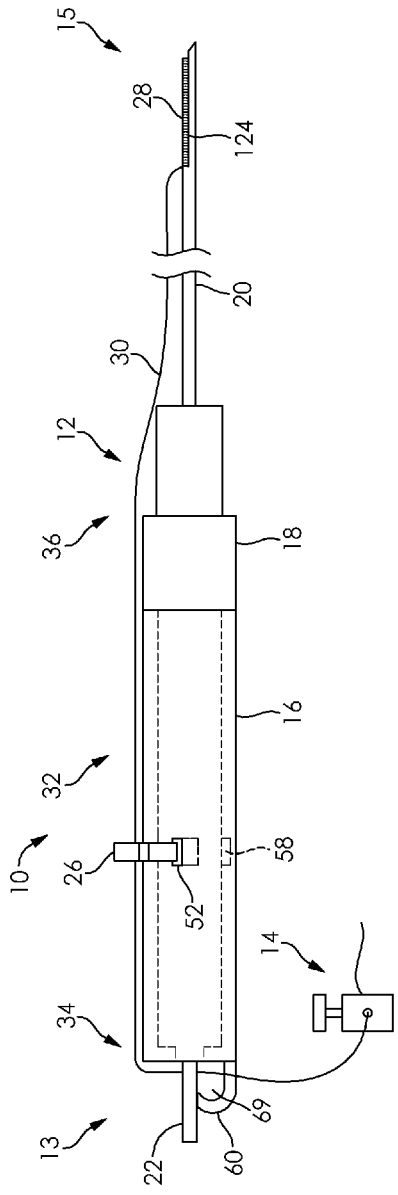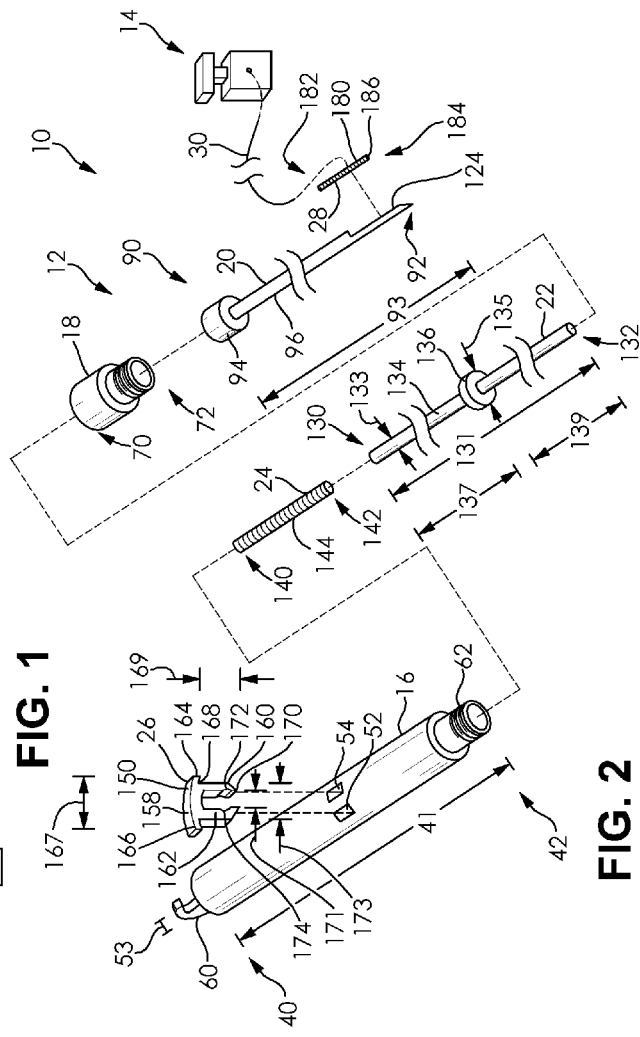
FIG. 1
FIG. 2

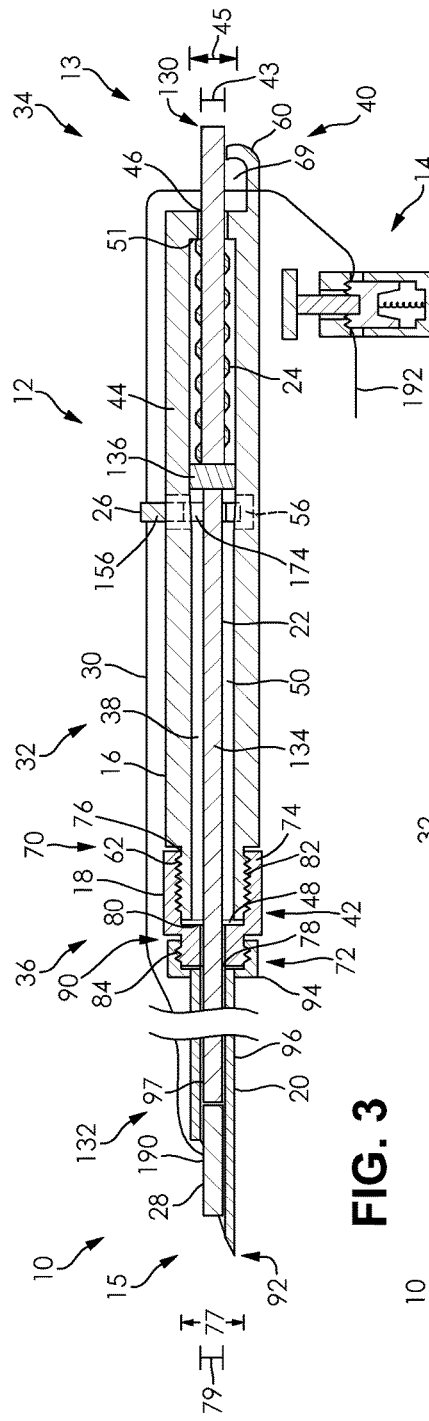

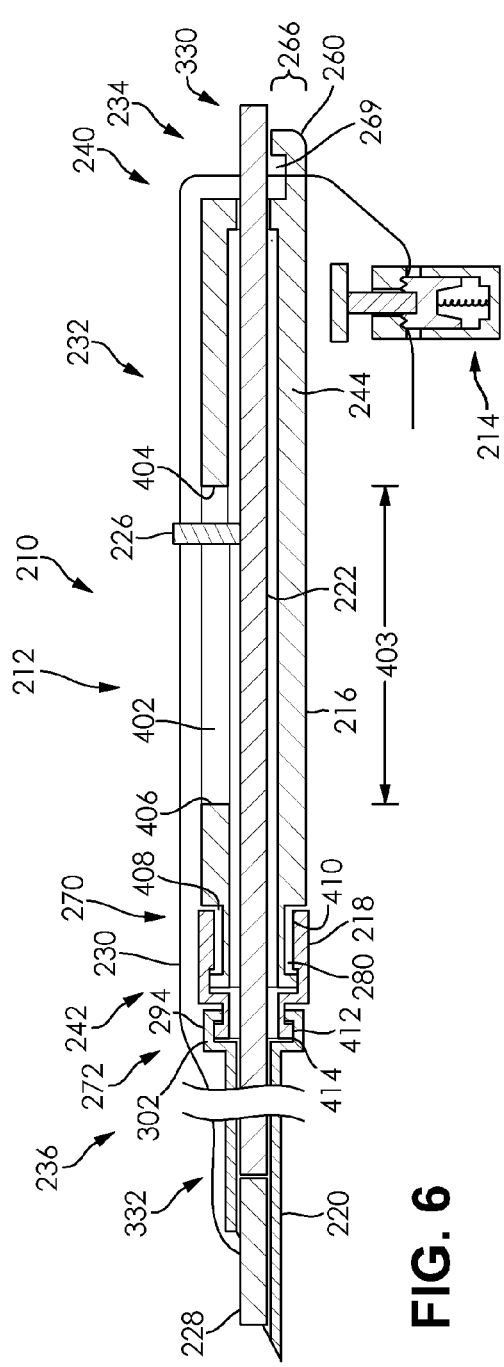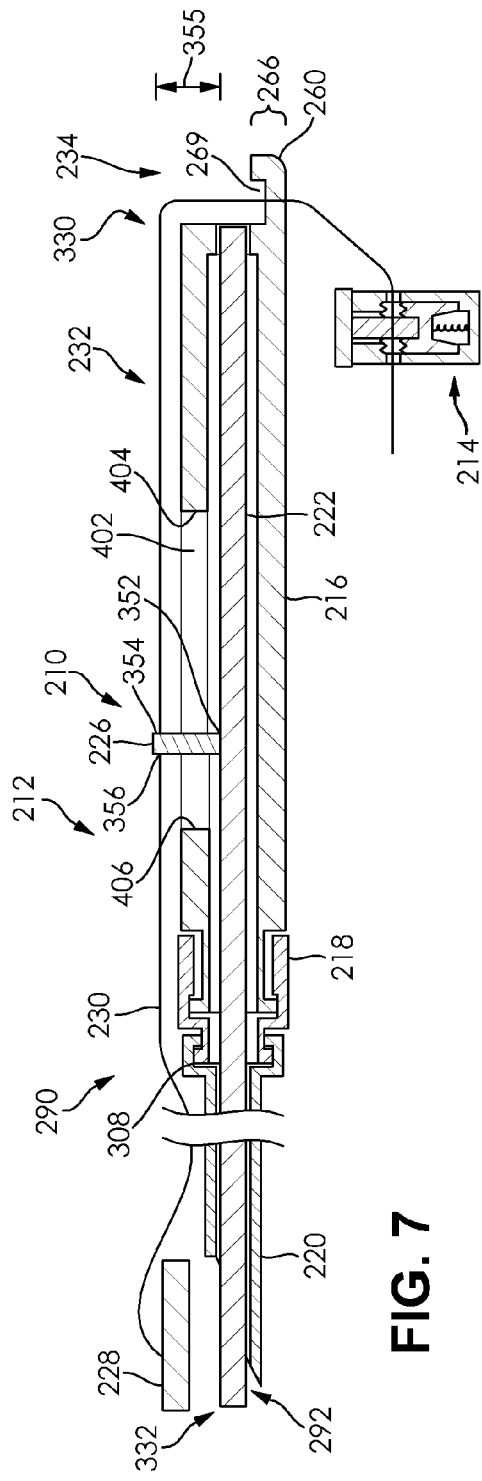

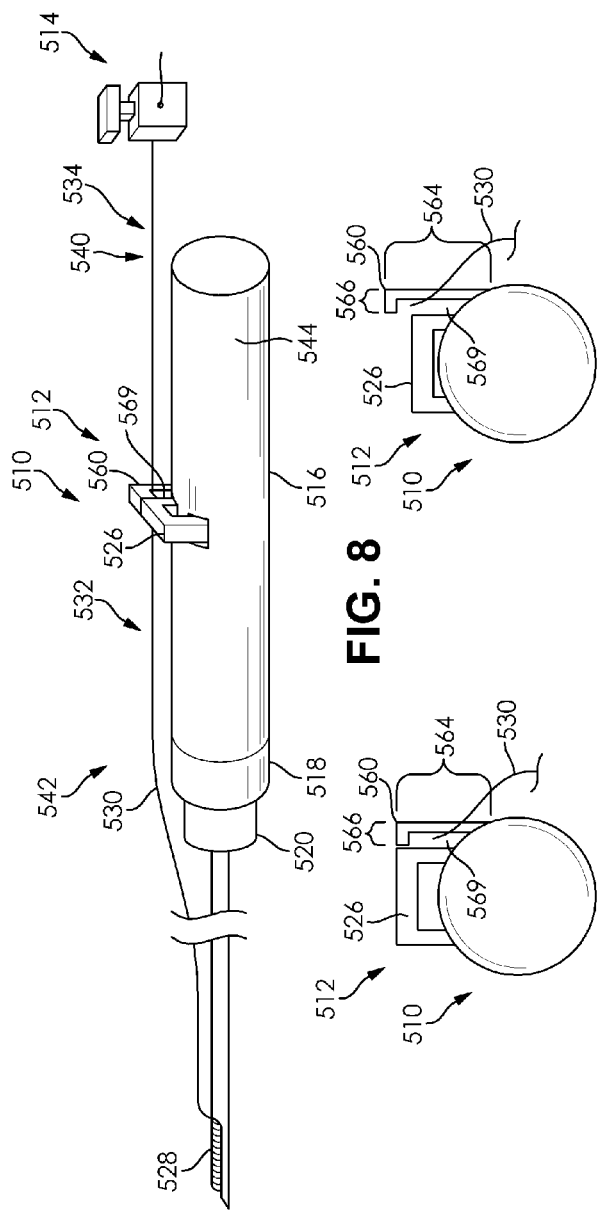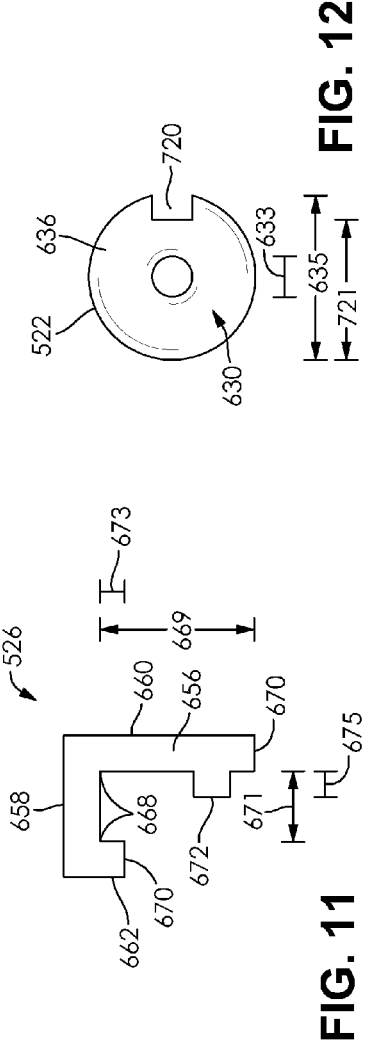

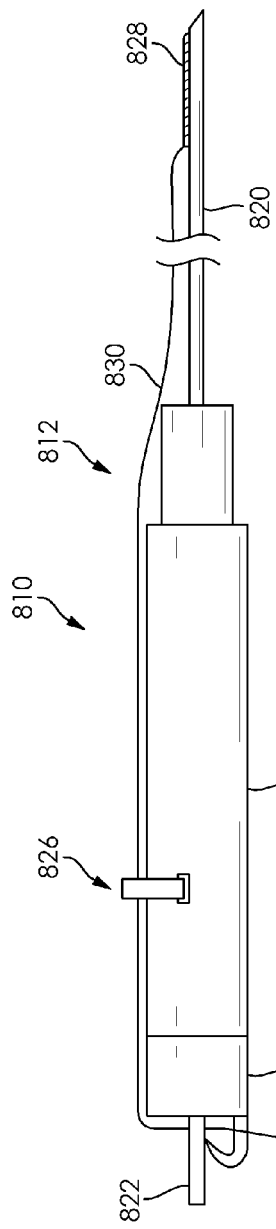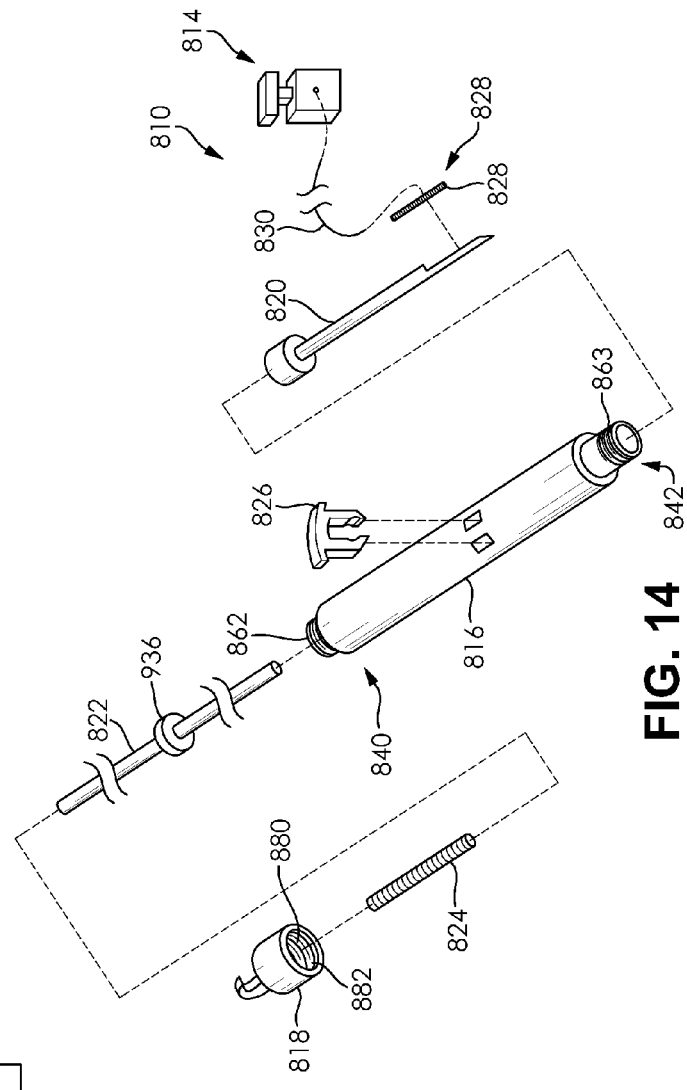

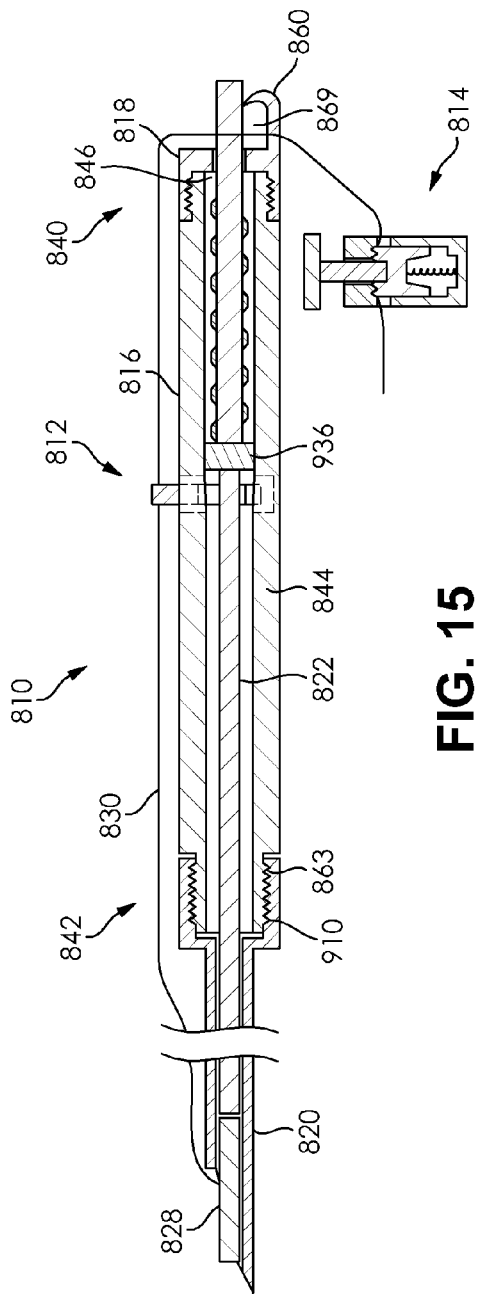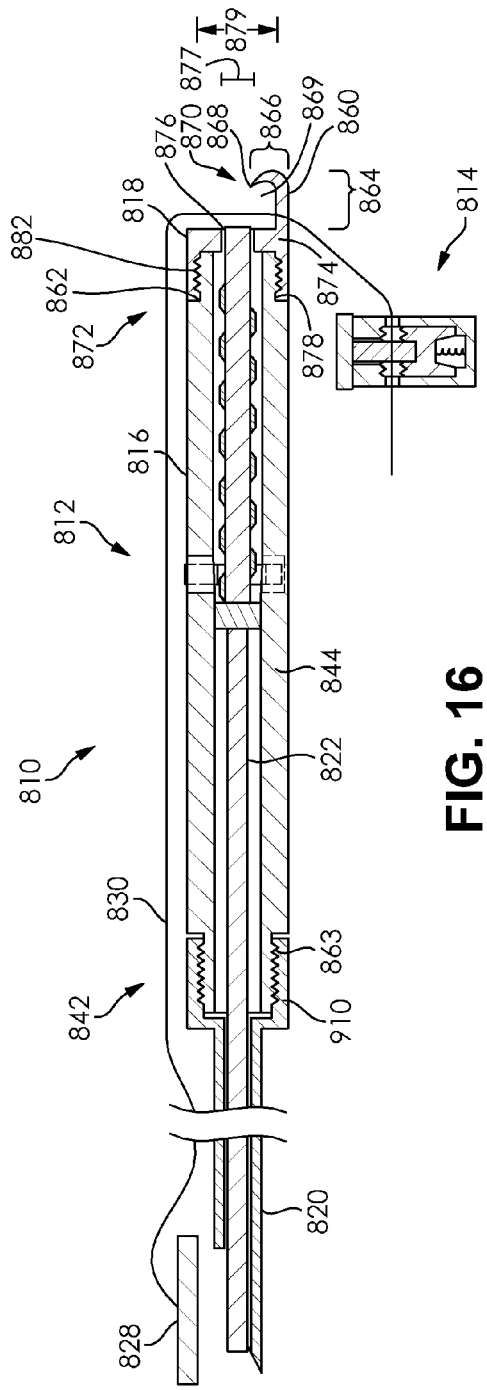

ANCHOR DEPLOYMENT SYSTEM, DEVICE, AND METHOD OF TREATMENT

RELATED APPLICATION

This application claims the benefit of U.S. Provisional Application No. 62/027,328, filed Jul. 22, 2014. The entire disclosure of this related application is hereby incorporated into this disclosure by reference.

FIELD

The disclosure relates generally to the field of medical systems, medical devices, and methods of treatment.

BACKGROUND

A variety of medical devices have been developed that are used to introduce an anchor at a point of treatment. For example, medical devices have been developed that are used to introduce an anchor into the stomach such that it can be drawn toward the abdominal wall using a suture or other structure. However, a need exists for improved medical devices that can be used to deploy an anchor at a point of treatment.

BRIEF DESCRIPTION OF THE DRAWINGS

FIG. 1 is a side view of an embodiment of an anchor deployment system that comprises an anchor deployment device, an anchor, a connector, and a retention mechanism.

FIG. 2 is a partially exploded perspective view of the anchor deployment system illustrated in FIG. 1.

FIG. 3 is a cross-sectional view of the anchor deployment system illustrated in FIG. 1 taken along the lengthwise axis of the anchor deployment device. Each of the anchor deployment device and the retention mechanism is shown in a first configuration.

FIG. 4 is a cross-sectional view of the anchor deployment system illustrated in FIG. 1 taken along the lengthwise axis of the anchor deployment device. Each of the anchor deployment device and the retention mechanism is shown in a second configuration.

FIG. 5 is a partial perspective view of another embodiment of an anchor deployment system that comprises an anchor deployment device, an anchor, a connector, and a retention mechanism.

FIG. 6 is a cross-sectional view of the anchor deployment system illustrated in FIG. 5 taken along the lengthwise axis of the anchor deployment device. Each of the anchor deployment device and the retention mechanism is shown in a first configuration.

FIG. 7 is a cross-sectional view of the anchor deployment system illustrated in FIG. 5 taken along the lengthwise axis of the anchor deployment device. Each of the anchor deployment device and the retention mechanism is shown in a second configuration.

FIG. 8 is a perspective view of another embodiment of an anchor deployment system that comprises an anchor deployment device, an anchor, a connector, and a retention mechanism.

FIG. 9 is a partial proximal end view of the anchor deployment system illustrated in FIG. 8. The anchor deployment device is shown in a first configuration.

FIG. 10 is a partial proximal end view of the anchor deployment system illustrated in FIG. 8. The anchor deployment device is shown in a second configuration.

FIG. 11 is a proximal end view of the actuator of the anchor deployment device illustrated in FIG. 8.

FIG. 12 is a proximal end view of the stylet of the anchor deployment device illustrated in FIG. 8.

FIG. 13 is a side view of another embodiment of an anchor deployment system that comprises an anchor deployment device, an anchor, a connector, and a retention mechanism.

FIG. 14 is a partially exploded perspective view of the anchor deployment system illustrated in FIG. 13.

FIG. 15 is a cross-sectional view of the anchor deployment system illustrated in FIG. 13 taken along the lengthwise axis of the anchor deployment device. Each of the anchor deployment device and the retention mechanism is shown in a first configuration.

FIG. 16 is a cross-sectional view of the anchor deployment system illustrated in FIG. 13 taken along the lengthwise axis of the anchor deployment device. Each of the anchor deployment device and the retention mechanism is shown in a second configuration.

DETAILED DESCRIPTION

Figure 17:
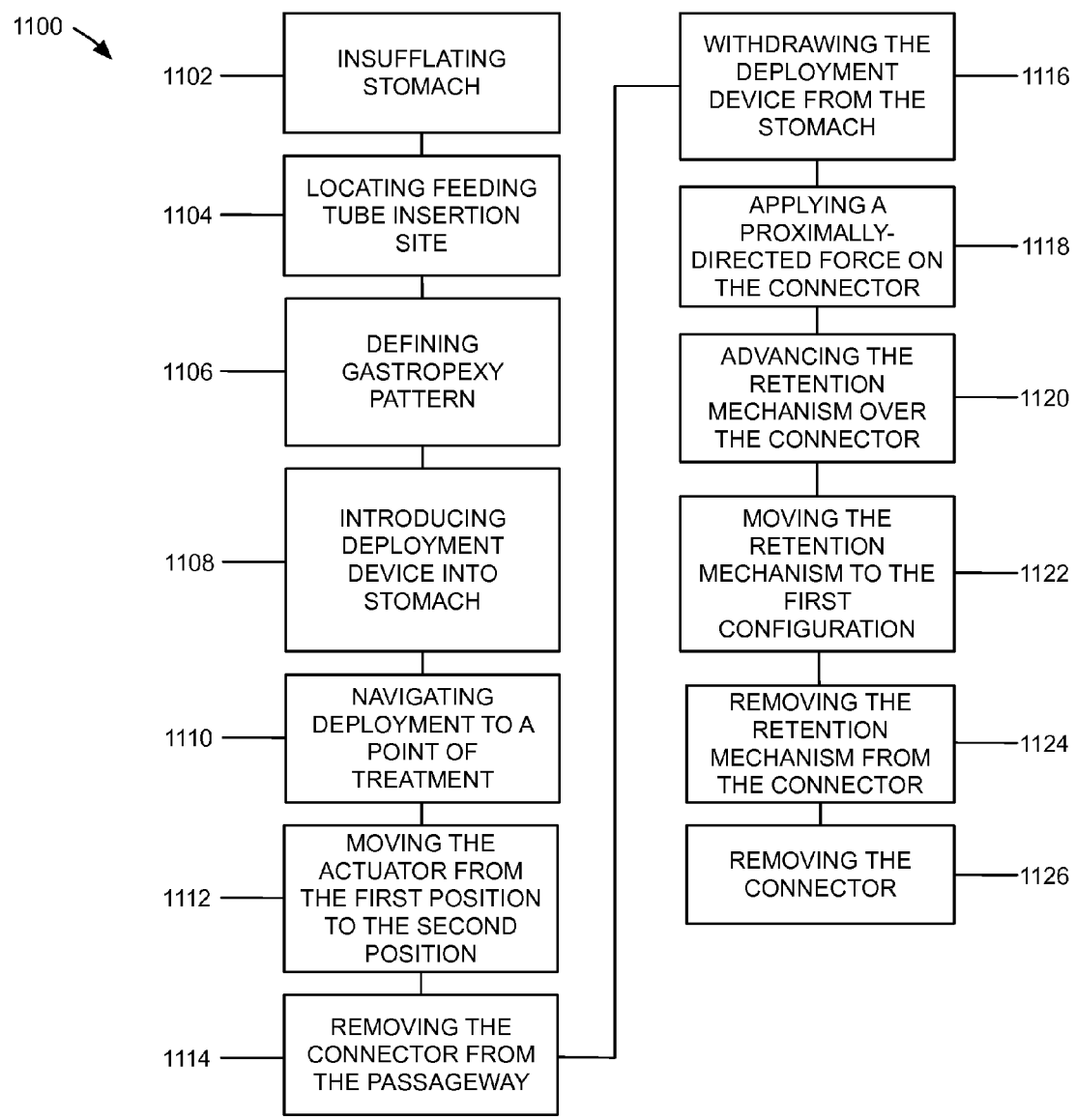
FIG. 17 is a flowchart representation of an example method of treatment.

The following detailed description and the appended drawings describe and illustrate various example embodiments of anchor deployment systems, anchor deployment devices, and methods of treatment. The description and illustration of these examples are provided to enable one skilled in the art to make and use an anchor deployment system, anchor deployment device, and to practice a method of treatment using an anchor deployment system or an anchor deployment device. They are not intended to limit the scope of the claims in any manner.

The use of "e.g.," "etc.," "for instance," "in example," and "or" and grammatically related terms indicate non-exclusive alternatives without limitation, unless otherwise noted. The use of "optionally" and grammatically related terms means that the subsequently described element, event, feature, or circumstance may or may not be present or occur, and that the description includes instances where said element, event, feature, or circumstance occurs and instances where it does not. The use of "attached" refers to the fixed, releasable, or integrated association of two or more elements and/or devices, unless otherwise noted. Thus, the term "attached" includes releasably attaching or fixedly attaching two or more elements and/or devices, unless otherwise noted. As used herein, the terms "proximal" and "distal" are used to describe opposing axial ends of the particular element or feature being described. The use of "diameter" refers to the length of a straight line passing from side to side through the center of a body, element, or feature, and does not impart any structural configuration on the body, element, or feature. The use of "circumference" refers to the distance around the exterior surface of a body, element, or feature, and does not impart any structural configuration on the body, element, or feature. The use of "bodily passage" or "body passage" refers to any passage within the body of an animal, including humans, and includes elongate passages, arteries, veins, and the stomach.

FIGS. 1, 2, 3, and 4 illustrate an embodiment of an anchor deployment system 10 that has an anchor deployment device 12, a retention mechanism 14, an anchor 28, and a connector 30. The anchor deployment device 12 has a proximal end 13, a distal end 15, a first handle portion 16, a second handle portion 18, an elongate member 20, a stylet 22, a spring 24, and an actuator 26. The anchor deployment device 12 is moveable between a first configuration and a second configuration. In the first configuration, the anchor 28 is disposed within the elongate member 20 and the connector 30 is releasably attached to the anchor deployment device 12, as shown in FIG. 3. In the second configuration, the anchor 28 is disposed exterior to the elongate member 20 and the connector 30 is removable from, or free of attachment to, the anchor deployment device 12, as shown in FIG. 4.

In the illustrated embodiment, the first handle portion 16 and the second handle portion 18 cooperatively define a handle 32 that has a proximal end 34, a distal end 36, and a lumen 38. The first handle portion 16 has a proximal end 40, a distal end 42, and a body 44 that defines a first opening 46, a second opening 48, a lumen 50, a shoulder 51, a first passageway 52, a second passageway 54, a first recess 56, a second recess 58, a protuberance 60, and threads 62. The first handle portion 16 has a length 41 that extends from the proximal end 40 to the distal end 42.

The first opening 46 is defined on the proximal end 40 and the second opening 48 is defined on the distal end 42. The lumen 50 extends from the first opening 46 to the second opening 48. Each of the first opening 46 and the lumen 50 has a first inside diameter 43 that is sized and configured to receive a portion of the stylet 22. Each of the second opening 48 and the lumen 50 has a second inside diameter 45 that is greater than the first inside diameter 43 and that is sized and configured to receive a portion of the stylet 22 and the projection 136 defined by the stylet 22, as described in more detail herein. The arrangement of the first inside diameter 43 and the second inside diameter 45 defines the shoulder 51 within the lumen 50 between the proximal end 40 and the distal end 42 of the first handle portion 16 which acts as a mechanical stop to proximal advancement of the stylet 22 and spring 24.

The first passageway 52 extends from an outer surface of the first handle portion 16 to the lumen 50. The second passageway 54 extends from an outer surface of the first handle portion 16 to the lumen 50. The first passageway 52 is defined on an axis that is disposed a distance from the lengthwise axis of the first handle portion 16 that is greater than one half of the diameter of a portion of the stylet 22 that extends from the projection 136 to the distal end 132 of the stylet 22. The second passageway 54 is defined on an axis that is disposed a distance from the lengthwise axis of the first handle portion 16 that is greater than one half of the diameter of a portion of the stylet 22 that extends from the projection 136 to the distal end 132 of the stylet 22. A length 53 of the first handle portion 16 is disposed between the first passageway 52 and the second passageway 54 that is greater than the diameter of a portion of the stylet 22 that extends from the projection 136 to the distal end 132 of the stylet 22.

Each of the first recess 56 and second recess 58 extends from an inner surface of the first handle portion 16 that defines a portion of the lumen 50 and toward the outer surface of the first handle portion 16. The first recess 56 is aligned with the first passageway 52 and the second recess 58 is aligned with the second passageway 54. Each of the first passageway 52, second passageway 54, first recess 56, and second recess 58 is in fluid communication with the lumen 50 and is sized and configured to receive a portion of one of the projections 160, 162 defined by the actuator 26, as described in more detail herein.

The protuberance 60 extends from the handle 32 and defines a first passageway wall that cooperatively defines a passageway 69 with a second passageway wall defined by the stylet 22, as described in more detail herein. The protuberance 60 has a first portion 64, a second portion 66, and a protuberance end 68. The first portion 64 extends from the proximal end 40 of the first handle portion 16 and away from the distal end 42. The second portion 66 extends from the first portion 64, toward the lengthwise axis of the first handle portion 16, and toward the distal end 42 of the first handle portion 16 to the protuberance end 68. In the illustrated embodiment, the protuberance 60 is hook-shaped such that it forms a first portion of a passageway wall that defines a passageway 69. Alternative embodiments can include a hook-shaped protuberance that does not extend toward the distal end of the first handle portion, such as the protuberance 260 illustrated in FIGS. 5, 6, and 7.

The threads 62 are disposed on an outer surface of the first handle portion 16 and extend from the distal end 42 toward the proximal end 40 of the first handle portion 16. The threads 62 define a helical structure that is sized and configured to interact with the helical structure defined by the first set of threads 82 defined on the second handle portion 18 such that the second handle portion 18 can be releasably attached to the first handle portion 16. Alternatively, the threads defined by a first handle portion can be disposed between the proximal end and the distal end of the first handle portion and/or on an inner surface of the first handle portion.

While the first handle portion 16 has been illustrated as defining threads 62 that are adapted to releasably attach the second handle portion 18 to the first handle portion 16, a first handle portion can include any suitable structure, connector, and/or adapter adapted to attach, or capable of attaching, one or more devices, or components, to the first handle portion. Skilled artisans will be able to select a suitable structure, connector, and/or adapter to include on a first handle portion according to a particular embodiment based on various considerations, including the material(s) that forms a second handle portion and/or an elongate member included in an anchor deployment device of which the first handle portion is a component. Example structures, connectors, and/or adapters considered suitable to include on a first handle portion include helical structures, morse tapers, connectors, luer lock connectors, Tuohy Borst adapters, and any other structure, connector, and/or adapter considered suitable for a particular embodiment.

While the first handle portion 16 has been illustrated as having a particular structural arrangement, a first handle portion can have any suitable structural arrangement. Skilled artisans will be able to select a suitable structural arrangement for a first handle portion according to a particular embodiment based on various considerations, including the structural arrangement of a second handle portion, elongate member, stylet, spring, and/or an actuator included in an anchor deployment device of which the first handle portion is a component. Example structural arrangements considered suitable for a first handle portion include first handle portions that define a slot alternative to first and second passageways (e.g., first handle portion 216), first handle portions that define a protuberance between the proximal end and the distal end of the handle (e.g., first handle portion 516), first handle portions that omit the inclusion of first and second recesses, first handle portions that omit the inclusion of a protuberance, and any other structural arrangement considered suitable for a particular embodiment. For example, the lumen defined by a first handle portion can be sized and configured such that an actuator can move between its first and second positions without the inclusion of first and second recesses.

In the illustrated embodiment, the second handle portion 18 is releasably attached to the first handle portion 16 and has a proximal end 70, a distal end 72, and a body 74 that defines a first opening 76, a second opening 78, a lumen 80, a first set of threads 82, and a second set of threads 84. The first opening 76 is defined on the proximal end 70 and the second opening 78 is defined on the distal end 72. The lumen 80 extends from the first opening 76 to the second opening 78. Each of the first opening 76 and the lumen 80 has a first inside diameter 77 that is sized and configured to receive a portion of the first handle portion 16. Each of the second opening 78 and the lumen 80 has a second inside diameter 79 that is less than the first inside diameter 77 and that is sized and configured to receive a portion of the stylet 22.

The first set of threads 82 is disposed on an inner surface of the second handle portion 18 that defines lumen 80 and extends from the proximal end 70 toward the distal end 72 of the second handle portion 18. The first set of threads 82 defines a helical structure that is sized and configured to interact with the helical structure defined by the threads 62 defined on the first handle portion 16 such that the second handle portion 18 can be releasably attached to the first handle portion 16. Alternatively, the first set of threads defined by a second handle portion can be defined between the proximal end and the distal end of the second handle portion and/or on an outer surface of the second handle portion.

The second set of threads 84 is disposed on an outer surface of the second handle portion 18 and extends from the distal end 72 toward the proximal end 70 of the second handle portion 18. The second set of threads 84 define a helical structure that is sized and configured to interact with the helical structure defined by the threads 110 defined on the elongate member 20 such that the elongate member 20 can be releasably attached to the second handle portion 18. Alternatively, the second set of threads defined by a second handle portion can be defined between the proximal end and the distal end of the second handle portion and/or on an inner surface of the second handle portion.

The first handle portion 16 and second handle portion 18 can be formed of any suitable material and skilled artisans will be able to select a suitable material to form a first handle portion and a second handle portion according to a particular embodiment based on various considerations, including the material(s) that forms an elongate member, stylet, spring, and/or an actuator included in an anchor deployment device of which the first handle portion and/or second handle portion are a component. Example materials considered suitable to form a first handle portion and/or a second handle portion include biocompatible materials, materials that can be made biocompatible, metals such as stainless steel, titanium, nickel-titanium alloy (e.g., Nitinol), thermoplastics, polymers, Pebax (Pebax is a registered trademark of Ato Chimie Corporation of Allee des Vosges, Courbevoie, France), nylon, polyethylene, high-density polyethylene (HDPE), high-performance polyethylene (HPPE), polyurethane, polyetheretherketone (PEEK), silicone, acrylonitrile butadiene styrene (ABS), polyoxymethylene (e.g., acetal), and any other material considered suitable for a particular embodiment.

While the second handle portion 18 has been illustrated as defining a first set of threads 82 and a second set of threads 84, a second handle portion can include any suitable structure, connector, and/or adapter adapted to attach, or capable of attaching, one or more devices, or components, to the second handle portion. Skilled artisans will be able to select a suitable structure, connector, and/or adapter to include on a second handle portion according to a particular embodiment based on various considerations, including the material(s) that forms a first handle portion, elongate member, stylet, spring, and/or an actuator included in an anchor deployment device of which the second handle portion is a component. Example structures, connectors, and/or adapters considered suitable to include on a second handle portion include helical structures, morse tapers, connectors, luer lock connectors, Tuohy Borst adapters, and any other structure, connector, and/or adapter considered suitable for a particular embodiment.

While an interlocking structure has been illustrated between the first handle portion 16 and the second handle portion 18, any suitable locking structure can be included on first handle portion and/or a second handle portion to provide releasable attachment between the first handle portion and the second handle portion. Skilled artisans will be able to select a suitable locking structure to include on a first handle portion and/or second handle portion according to a particular embodiment based on various considerations, including the material(s) that forms the first handle portion and second handle portion. Example locking structures considered suitable include interlocking structures, structures that provide a friction fit between the first handle portion and the second handle portion, structures that provide a snap fit between the first handle portion and the second handle portion, threaded connections, mechanical fasteners, and any other structure considered suitable for a particular embodiment. Alternative embodiments can omit the inclusion of a second handle portion such that an elongate member is releasably attached to the distal end of the first handle portion using any of the structures, connectors, adapters, or locking structures described herein.

In the illustrated embodiment, the elongate member 20 has a proximal end 90, a distal end 92, a hub 94, and a shaft 96. The elongate member 20 has a length 93 that extends from the proximal end 90 to the distal end 92. The hub 94 and the shaft 96 cooperatively define an elongate member lumen 97. The hub 94 is attached to the shaft 96 such that the elongate member 20 can be releasably attached to another component, such as the second handle portion 18.

The hub 94 has a proximal end 98, a distal end 100, and a body 102 that defines a first opening 104, a second opening 106, lumen 108, and threads 110. The first opening 104 is defined on the proximal end 98 and the second opening 106 is defined on the distal end 100. The lumen 108 extends from the first opening 104 to the second opening 106 and defines a first portion of the lumen 97 of the elongate member 20. The first opening 104 has a first inside diameter 105 that is sized and configured to receive a portion of the second handle portion 18. Alternatively, the first inside diameter can be sized and configured to receive a portion of the first handle portion. The second opening 106 has a second inside diameter 107 that is less than the first inside diameter 105 and that is sized and configured to receive a portion of the stylet 22.

The threads 110 are disposed on an inner surface of the hub 94 that defines the lumen 108 and extend from the proximal end 98 of the hub 94 toward the distal end 100. Alternatively, the threads defined by a hub can be disposed between the proximal end and the distal end of the hub and/or defined on an outer surface of the hub. The threads 110 define a helical structure that is sized and configured to interact with the helical structure defined by the second set of threads 84 defined on the second handle portion 18 such that the elongate member 20 can be releasably attached to the second handle portion 18. Alternatively, the threads defined by an elongate member can be sized and configured to interact with the threads defined by a first handle portion such that the elongate member can be releasably attached to the first handle portion.

The shaft 96 has a proximal end 112, a tapered distal end 114, and a body 116 that defines a first opening 118, a second opening 120, a lumen 122, and a slot 124. The first opening 118 is disposed on the proximal end 112 and the second opening 120 is disposed on the distal end 114. The lumen 122 extends from the first opening 118 to the second opening 120 and defines a second portion of the lumen 97 of the elongate member 20. Each of the first opening 118, second opening 120, and lumen 122 has an inside diameter 119 that is sized and configured to receive a portion of the stylet 22. The slot 124 extends from the distal end 114 toward the proximal end 112 and is defined along a portion of the circumference of the shaft 96. Thus, the slot 124 interrupts a portion of the circumference of the shaft 96 and provides access to the lumen 122. The slot 124 is sized and configured to receive a portion of the connector 30. Alternatively, a slot can be sized and configured to receive a portion of an anchor.

The elongate member 20 can be formed of any suitable material and skilled artisans will be able to select a suitable material to form an elongate member according to a particular embodiment based on various considerations, including the material(s) that forms a first handle portion, second handle portion, actuator, spring, and/or an anchor included in an anchor deployment device of which the elongate member is a component. Example materials considered suitable to form an elongate member include biocompatible materials, materials that can be made biocompatible, metals such as stainless steel, titanium, nickel-titanium alloy (e.g., Nitinol), thermoplastics, polymers, Pebax (Pebax is a registered trademark of Ato Chimie Corporation of Allee des Vosges, Courbevoie, France), nylon, polyethylene, high-density polyethylene (HDPE), high-performance polyethylene (HPPE), polyurethane, polyetheretherketone (PEEK), silicone, acrylonitrile butadiene styrene (ABS), polyoxymethylene (e.g., acetal), and any other material considered suitable for a particular application. In the illustrated embodiment, the hub 94 is formed of a first material and the shaft 96 is formed of a second material. The first material is different than the second material. In the embodiment shown, the first material is a polymer and the second material is a metal. However, alternative embodiments can include an elongate member that has a hub and a shaft that are formed of the same material.

While the elongate member 20 has been illustrated as having threads 110, an elongate member can include any suitable structure, connector, and/or adapter adapted to attach, or capable of attaching, one or more devices, or components, to the elongate member. Skilled artisans will be able to select a suitable structure, connector, and/or adapter to include on an elongate member according to a particular embodiment based on various considerations, including the material(s) that forms a first handle portion and/or a second handle portion included in an anchor deployment device of which the elongate member is a component. Example structures, connectors, and/or adapters considered suitable to include on an elongate member include helical structures, morse tapers, connectors, luer lock connectors, Tuohy Borst adapters, and any other structure, connector, and/or adapter considered suitable for a particular embodiment.

While an interlocking structure has been illustrated between the elongate member 20 and the second handle portion 18, any suitable locking structure can be included on an elongate member and/or a second handle portion to provide releasable attachment between the elongate member and second handle portion. Skilled artisans will be able to select a suitable locking structure to include on an elongate member and/or second handle portion according to a particular embodiment based on various considerations, including the material(s) that forms the elongate member and the second handle portion. Example locking structures considered suitable include interlocking structures, structures that provide a friction fit between the elongate member and the second handle portion, structures that provide a snap fit between the elongate member and the second handle portion, threaded connections, mechanical fasteners, and any other structure considered suitable for a particular embodiment.

In the illustrated embodiment, the stylet 22 is partially disposed within the handle 32 (e.g., first handle portion 16 and second handle portion 18) and the elongate member 20 and is moveable relative to the handle 32 between a first position, as shown in FIG. 3, and a second position, as shown in FIG. 4. The stylet 22 has a proximal end 130, a distal end 132, and a body 134 that defines a projection 136 that is moveably disposed within the lumen 50 defined by the first handle portion 16. The stylet 22 has a length 131 that extends from the proximal end 130 to the distal end 132. The length 131 of the stylet 22 is greater than the length 41 of the first handle portion 16 and the length 93 of the elongate member 20.

The proximal end 130 of the stylet 22 has a first outside diameter 133 that is less than the first inside diameter 43 of the first opening 46 defined by the first handle portion 16. The projection 136 has a second outside diameter 135 that is greater than the first outside diameter 133 and greater than the first inside diameter 43 of the first opening 46 defined by the first handle portion 16. In addition, the second outside diameter 135 is less than the second inside diameter 45 of the lumen 50 defined by the first handle portion 16 and greater than the second inside diameter 79 defined by the second handle portion 18. This configuration provides structure that retains the projection 136 within the lumen 50 defined by the first handle portion 16.

The stylet 22 has a first portion that extends from the projection 136 to the proximal end 130 of the stylet 22. The first portion of the stylet 22 has a first length 137. The stylet 22 has a second portion that extends form the projection 136 to the distal end 132 of the stylet 22. The second portion has a second length 139. The first length 137 has a value that positions the proximal end 130 of the stylet 22 at the protuberance end 68 defined by the handle 32 when the stylet 22 is in the first position, as shown in FIG. 3, and positions the proximal end 130 of the stylet 22 distal to the protuberance end 68 (e.g., between the protuberance end 68 and the distal end 42 of the first handle portion 16) when the stylet 22 is in the second position, as shown in FIG. 4. Alternatively, the first length of a stylet can have a value that positions the proximal end of the stylet proximal to, near, or adjacent to the end of protuberance when the stylet is in the first position.

The second length 139 has a value that positions the distal end 132 of the stylet 22 proximal to the distal end 92 of the elongate member 20 when the stylet 22 is in the first position, as shown in FIG. 3, and positions the distal end 132 of the stylet 22 at the distal end 92 of the elongate member 20 when the stylet 22 is in the second position, as shown in FIG. 4. This provides a mechanism to blunt the distal end 15 of the deployment device 12 when the stylet 22 is in the second position. Thus, when the stylet 22 is in the first position the distal end 15 of the deployment device 12 has a pointed, or sharp, distal end 15 and when the stylet 22 is in the second position the distal end 15 of the deployment device 12 is blunt, or pointless. In the illustrated embodiment, when the stylet 22 is in the first position it contacts the proximal end 182 of the anchor 28. Alternative embodiments, however, can include a stylet that has a second length that positions the distal end of the stylet proximal to the proximal end of the anchor when the stylet is in the first position. Alternatively, the second length can have a value that positions the distal end of the stylet distal to, proximal to, adjacent, or near, the distal end of an elongate member when the stylet is in the second position.

In the illustrated embodiment, the portion of the body 134 of the stylet 22, a dynamic member, that extends proximal to the proximal end 34 of the handle 32 defines a second passageway wall that cooperatively defines the passageway 69 with the first passageway wall defined by the handle 32 (e.g., protuberance 60). In use, when the stylet 22 is in the first position the passageway 69 is circumferentially closed such that the connector 30 is releasably attached to the handle 32 (e.g., first handle portion 16) and when the stylet 22 is in the second position the passageway 69 is circumferentially open such that the connector 30 can be removed from the passageway 69. Therefore, the passageway 69 is temporary and the configuration of its circumference is based on the position of the dynamic member (e.g., stylet, actuator).

The stylet 22 can be formed of any suitable material and skilled artisans will be able to select a suitable material to form a stylet according to a particular embodiment based on various considerations, including the material(s) that forms a first handle portion, second handle portion, elongate member, actuator, spring, and/or an anchor included in an anchor deployment device of which the stylet is a component. Example materials considered suitable to form a stylet include biocompatible materials, materials that can be made biocompatible, metals such as stainless steel, titanium, nickel-titanium alloy (e.g., Nitinol), thermoplastics, polymers, Pebax (Pebax is a registered trademark of Ato Chimie Corporation of Allee des Vosges, Courbevoie, France), nylon, polyethylene, high-density polyethylene (HDPE), high-performance polyethylene (HPPE), polyurethane, polyetheretherketone (PEEK), silicone, acrylonitrile butadiene styrene (ABS), polyoxymethylene (e.g., acetal), and any other material considered suitable for a particular application.

While the projection 136 has been illustrated as having a particular structural configuration and as being defined by the body 134 of the stylet 22, a projection can have any suitable structural configuration and can alternatively be a separate component attached to a stylet using any suitable technique or method of attachment. Example structural configurations considered suitable for a projection include projections that are cylindrical, such as projection 136, spherical, semi-spherical, and any other configuration considered suitable for a particular embodiment. In embodiments in which the projection of a stylet comprises a separate component, the projection can be formed of the same material that forms the stylet or can be formed of a material that is different than the material that forms the stylet. For example, a stylet can be formed of a metal, such as those described herein, and the projection can be formed of a polymer, such as those described herein. The projection can be positioned on the stylet and attached using any suitable technique or method, such as using threaded components and/or adhesives.

In the illustrated embodiment, the spring 24 is disposed within the lumen 50 defined by the first handle portion 16 between the shoulder 51 and the projection 136 defined by the stylet 22. The spring 24 has a proximal end 140, a distal end 142, and a body 144 that defines a helical configuration that extends from the proximal end 140 to the distal end 142. The spring 24 has a compressed configuration, as shown in FIG. 3, when the stylet 22 and the actuator 26 are in the first position and an expanded configuration, as shown in FIG. 4, when the stylet 22 and the actuator 26 are in the second position. The spring 24 is configured to bias the stylet 22 to the second position when the stylet 22 (e.g., projection 136) is free of contact with the actuator 26 and the actuator 26 is in the second position. Alternatively, the body of a spring can define a helical configuration that is disposed between the proximal end and the distal end of the spring, that extends from the proximal end toward the distal end, or that extends from the distal end toward the proximal end. In the illustrated embodiment, the spring 24 is a compression spring, which exerts a force resisting compression proportional to the distance the spring has been compressed.

While the spring 24 has been described as a particular type of spring, any suitable spring, formed of any suitable material, and having any suitable compressed and/or uncompressed lengths is considered suitable. Skilled artisans will be able to select a suitable spring, material to form a spring, and suitable compressed and/or uncompressed lengths for a spring according to a particular embodiment based on various considerations, including the length of a handle relative to the length of a stylet.

In the illustrated embodiment, the actuator 26 is partially disposed within the handle 32 and is moveable relative to the handle 32 between a first position, as shown in FIG. 3, and a second position, as shown in FIG. 4. In the illustrated embodiment, the actuator 26 is a depressible member 150 that can be advanced into, and out of, the first and second passageways 52, 54 defined by the first handle portion 16. However, while a depressible member 150 has been illustrated, a deployment device can include any suitable actuator capable of actuating movement of a stylet between a first position and a second position. Skilled artisans will be able to select a suitable actuator to include in an anchor deployment device according to a particular embodiment based on various considerations, including the structural arrangement of the handle and/or the stylet. Example actuators considered suitable to include in an anchor deployment device include depressible members, rotatable members, slidable members, linear actuators, pivotable actuators, levers, and any other actuator considered suitable for a particular embodiment.

The actuator 26 has a proximal end 152, a distal end 154, and an actuator body 156 that defines a top member 158, a first projection 160, and a second projection 162. The top member 158 extends from a first end 164 to a second end 166 and has a length 167 that extends from the first end 164 to the second end 166. The length 167 of the top member 158 is greater than the sum of the diameter of the first passageway 52, the diameter of the second passageway 54, and the length 53 of the first handle portion 16 disposed between the first passageway 52 and the second passageway 54. This structural arrangement provides a mechanical stop to advancement of the actuator 26 into the lumen 50 defined by the first handle portion 16.

Each of the first projection 160 and second projection 162 has a first end 168 attached to the top member 156 and a second end 170. Each of the first and second projections 160, 162 has a length 169 that extends from the first end 168 to the second end 170. In the illustrated embodiment, the lengths 169 of the first and second projections 160, 162 are equal. However, alternative embodiments can include a first projection that has a length that is different than the length of a second projection. The first projection 160 is separated from the second projection 162 by a distance 171 that is less than the outside diameter 135 of the projection 136 defined by the stylet 22. This structural arrangement provides a mechanical stop to distal advancement of the stylet 22 within the lumen 50 defined by the first handle portion 16 when the actuator 26 is in the first position.

The actuator body 156 defines a first notch 172 on the first projection 160 that extends from a surface directed toward the second projection 162, into the first projection 160, and away from the second projection 162. The actuator body 156 defines a second notch 174 on the second projection 162 that extends from a surface directed toward the first projection 160, into the second projection 162, and away from the first projection 160. The first notch 172 defines a curved surface on the first projection 168 that corresponds to a portion of the outer surface of the projection 136. The second notch 174 defines a curved surface on the second projection 170 that corresponds to a portion of the outer surface of the projection 136. A distance 173 that is greater than the outside diameter 135 of the projection 136 defined by the stylet 22 separates the surfaces created by the notches 172, 174. This structural arrangement allows the stylet 22 to advance beyond the actuator 26 in a distal direction through the lumen 50 defined by the first handle portion 16 when the actuator 16 is in the second position.

The first and second projections 160, 162 are sized and configured to maintain the position of the stylet 22 when the projection 136 is disposed between the actuator 26 and the proximal end 40 of the first handle portion 16. The surfaces created by the notches 172, 174 are sized and configured to allow the projection 136 to pass through the actuator 26 when the actuator 26 moves to the second position and the notches 172, 174 are aligned with the projection 136. The structural arrangement defined by the notches 172, 174 defines a first keyed structure that corresponds to a second keyed structure defined by the projection 136 of the stylet 22 such that when the actuator 26 is in the first position the stylet 22 is in the first position and contacts the actuator 26 and when the actuator 26 is in the second position the stylet 22 can advance to the second position (e.g., via the force being applied to the projection 136 by the spring 24).

The actuator 26 can be formed of any suitable material and skilled artisans will be able to select a suitable material to form an actuator according to a particular embodiment based on various considerations, including the material(s) that forms a first handle portion, second handle portion, stylet, spring, and/or an anchor included in an anchor deployment device of which the actuator is a component. Example materials considered suitable to form an actuator include biocompatible materials, materials that can be made biocompatible, metals such as stainless steel, titanium, nickel-titanium alloy (e.g., Nitinol), thermoplastics, polymers, Pebax (Pebax is a registered trademark of Ato Chimie Corporation of Allee des Vosges, Courbevoie, France), nylon, polyethylene, high-density polyethylene (HDPE), high-performance polyethylene (HPPE), polyurethane, polyetheretherketone (PEEK), silicone, acrylonitrile butadiene styrene (ABS), polyoxymethylene (e.g., acetal), and any other material considered suitable for a particular application.

While the actuator 26 has been illustrated as having a particular structural arrangement, an actuator can have any suitable structural arrangement and skilled artisans will be able to select a suitable structural arrangement for an actuator according to a particular embodiment based on various considerations, including the structural arrangement of a projection defined by a stylet. For example, while the actuator 26 has been illustrated as defining notches 172, 174 that allow the projection 136 defined by the stylet 22 to advance through the actuator 26, an actuator body can define any suitable keyed structure that corresponds to a keyed structure defined by a projection on a stylet. For example, an actuator can include any suitable number of notches on one or more projections or can alternatively define one or more protuberances on or more projections that extend from a projection and are sized and configured to pass through one or more notches defined by a projection defined by a stylet. Any suitable structure capable of maintaining the position of a stylet when an actuator is in the first position and allowing the stylet to move within the handle when the actuator is in the second position can be used. While the actuator body 156 has been illustrated as defining a plurality of projections 160, 162, an actuator body can define any suitable number of projections, such as one, at least one, two, a plurality, three, four, five, six, and any other number considered suitable for a particular embodiment.

While the notches 172, 174 have been illustrated as defining a curved surface on the first and second projections 160, 162 that corresponds to a portion of the outer surface of the projection 136, a notch defined by the body of an actuator can define any suitable type of surface on a projection. Skilled artisans will be able to select a suitable surface for a notch to define on a projection according to a particular embodiment based on various considerations, including the structural arrangement of a projection defined by a stylet. Examples of surfaces considered suitable for a notch to define on a projection include surfaces that are planar, curved, multifaceted, and any other surface considered suitable for a particular embodiment.

In the illustrated embodiment, the anchor 28 is a flexible bar member 180 that can be disposed within, and withdrawn from, the lumen 97 defined by the elongate member 20. The anchor 28 has a proximal end 182, a distal end 184, and a body 186. The anchor 28 has a length 183 that extends from the proximal end 182 to the distal end 184. Optionally, an anchor can be omitted from an anchor deployment system and provided separately.

The anchor 28 can be formed of any suitable material and have any suitable structure, and skilled artisans will be able to select a suitable material to form an anchor and a suitable structure for an anchor according to a particular embodiment based on various considerations, including the procedure intended to be performed. Example materials considered suitable to form an anchor include biocompatible materials, materials that can be made biocompatible, biological materials, bioabsorbable materials, non-bioabsorbable materials, metals such as stainless steel, titanium, nickel-titanium alloy (e.g., Nitinol), thermoplastics, polymers, Pebax (Pebax is a registered trademark of Ato Chimie Corporation of Allee des Vosges, Courbevoie, France), nylon, polyethylene, high-density polyethylene (HDPE), high-performance polyethylene (HPPE), polyurethane, polyetheretherketone (PEEK), silicone, acrylonitrile butadiene styrene (ABS), polyoxymethylene (e.g., acetal), and any other material considered suitable for a particular application.

While anchor 28 has been illustrated as a bar member 180, an anchor deployment system can include any suitable anchor capable of being disposed within a bodily passage, such as the stomach, and that can be used to treat the bodily passage, such as by being used in combination with a connector to draw the stomach toward the abdominal wall. Skilled artisans will be able to select a suitable anchor to include in an anchor deployment system according to a particular embodiment based on various considerations, including the structural arrangement of an elongate member, and/or a stylet. Example anchors considered suitable to include in an anchor deployment system include T-bar anchors, T-tag anchors, elongated rods, bar members, bar members that include a helical spring sheath, and any other anchor considered suitable for a particular embodiment. For example, any anchor capable of anchoring the end portion of a connector against a tissue wall (e.g., when tensioning the connector to draw first and second tissues toward one another) is considered suitable, such as anchors used in gastropexy procedures.

In the illustrated embodiment, the connector 30 has a first end 190, a second end 192, and a length that extends from the first end 190 to the second end 192. A portion of the connector 30 that extends from the first end 190 toward the second end 192 is attached to the anchor 28 and a portion of the length of the connector 30 is positioned within the retention mechanism 14, as described in more detail herein. The connector 30 extends from the first end 190 through the passageway 69 cooperatively defined by the handle 32 (e.g., first handle portion 16), a static member, and the stylet 22, the dynamic member, such that the connector 30 is releasably attached to the handle 32 when the stylet 22 and the actuator 26 are in the first position. The connector 30 is removable from the handle 32 when the stylet 22 and the actuator 26 are in the second position. Optionally, a connector can be omitted from an anchor deployment system and provided separately.

The portion of the connector 30 attached to the anchor 28 can be attached to any suitable portion of the anchor 28, at any suitable location, and using any suitable method of attachment (e.g., tying the connector to the anchor, using adhesives, welding). For example, the portion of the connector 30 attached to the anchor 28 can be attached at the proximal end 182, the distal end 184, or between the proximal end 182 and the distal end 184 of the anchor 28. In the illustrated embodiment, the connector 30 is attached between the proximal end 182 and the distal end 184 of the anchor 28. In the illustrated embodiment, when the stylet 22 is in the first position, as shown in FIG. 3, the connector 30 is disposed at the proximal end of the slot 124 and the distal end 184 of the anchor 28 is disposed proximal to the distal end 92 of the elongate member 20 (e.g., between the proximal end 90 and the distal end 92 of the elongate member 20) such that it does not extend beyond the distal end 92 of the elongate member 20. Alternatively, an anchor can be disposed within an elongate member such that the distal end of the anchor is disposed at, near, about, or distal to the distal end of the elongate member when a stylet is in the first position and/or a connector can be disposed distal to, near, or about the proximal end of the slot when the stylet is in the first position.

The connector 30 can be formed of any suitable material and can have any suitable length, stiffness, and any suitable cross-sectional configuration. Skilled artisans will be able to select a suitable material to form a connector and a suitable length, cross-sectional configuration, and stiffness for a connector according to a particular embodiment based on various considerations, including the material(s) that forms a first handle portion, second handle portion, stylet, actuator, and/or an anchor included in an anchor deployment device of which the connector is a component. Example materials considered suitable to form a connector include biocompatible materials, materials that can be made biocompatible, biological materials, bioabsorbable materials, non-bioabsorbable materials, polymers, nylon, polyester, polypropylene, connectors that include antimicrobial materials, bioabsorbable materials, polyglycolic acid, polylactic acid, polydioxanone, and any other material considered suitable for a particular application. A connector can comprise a monofilament connector or a multi-filament connector. Commercially available sutures (e.g., monofilament, multi-filament), coils, thread-like structures, and lengths of wire are examples of connectors considered suitable to include in an anchor deployment system, such as those described herein. A connector can be formed of a material that has a stiffness that is relatively more rigid or relatively more flexible than the material that forms an anchor included in an anchor deployment system. In the illustrated embodiment, the connector is formed of a material that is relatively more flexible than the material that forms the anchor. Example lengths considered suitable for a connector include lengths between about 1 centimeter and about 100 centimeters, lengths that are equal to, substantially equal to, less than, greater than, or about 1 centimeter, 10 centimeters, 20 centimeters, 30 centimeters, 40 centimeters, and 50 centimeters, and any other length considered suitable for a particular embodiment. The inventor has determined that connectors that have a length of about 20 centimeters are suitable to include in an anchor deployment system. Example diameters considered suitable for a connector include diameters between about 0.01 millimeters and about 0.8 millimeters, diameters that are equal to, substantially equal to, less than, greater than, or about 0.01 millimeters, 0.2 millimeters, 0.3 millimeters, 0.35 millimeters, 0.4 millimeters, and 0.5 millimeters, and any other diameter considered suitable for a particular embodiment. The inventor has determined that connectors that have a diameter between about 0.2 millimeters and about 0.3 millimeters are suitable to include in an anchor deployment system.

The retention mechanism 14 can comprise any device capable of being releasably attached to the connector 30 and that can be used to secure the anchor 28 and the connector 30 at a point of treatment, such as against the stomach when a gastropexy is being performed. Example retention mechanisms considered suitable to include in a deployment system include any of the retention devices described in U.S. Nonprovisional patent application Ser. No. 13/766,084, filed Feb. 13, 2013, which is hereby incorporated by reference into this disclosure in its entirety. In the illustrated embodiment, the retention mechanism 14 is disposed along the length of the connector 30 and is moveable between a first configuration in which the retention mechanism 14 is releasably attached to the connector 30, as shown in FIG. 3, and a second configuration in which the retention mechanism 14 is free of attachment to the connector 30 and can move along the length of the connector 30, as shown in FIG. 4. When the retention mechanism 14 is in the first configuration it is fixed along the length of the connector 30. Optionally, a retention mechanism can be omitted from an anchor deployment system and provided separately.

The deployment device 12 is assembled by advancing the spring 24 into the lumen 50 defined by the first handle portion 16 and subsequently introducing the proximal end 130 of the stylet 22 into the lumen 50. A proximally-directed force is then applied on the stylet 22 until the projection 136 defined by the stylet 22 is disposed between the first and second passageways 52, 54 and the proximal end 40 of the first handle portion 16. The actuator 26 is then introduced into the first and second passageways 52, 54 until the first and second projections 160, 162 are disposed distal to the projection 136 defined by the stylet 22, as shown in FIG. 3. The actuator 26 is positioned in its first position such that the projection 136 is unable to move distally beyond the actuator 26. This configuration positions the stylet 22 in its first position. When the stylet 22 is in its first position, the spring 24 is in its compressed configuration such that the proximal end 140 of the spring 24 contacts the shoulder 51 defined by the first handle portion 16 and the distal end 142 of the spring 24 contacts the projection 136 defined by the stylet 22. When in the compressed configuration, the spring 24 biases the stylet 22 toward its second position such that it contacts the actuator 26. The second handle portion 18 is then releasably attached to the first handle portion 16 and the elongate member 20 is releasably attached to the second handle portion 18. The connector 30 can be attached to the anchor 28 at any suitable time and the anchor 28 can be positioned within the lumen 97 defined by the elongate member 20 at any suitable time. The connector 30 can be passed through the passageway 69 defined by the handle 32 and the stylet 22 and then the retention mechanism 14 can be releasably attached to the connector 30. Alternatively, the connector 30 can be disposed within the passageway 69 prior to the stylet 22 being introduced into the lumen 50 define by the first handle portion 16.

In use, when it is desired to deploy the anchor 28, a user applies a force on the actuator 26 in a direction toward the handle 32 until the first and second notches 172, 174 are aligned with the projection 136 defined by the stylet 22. Once the first and second notches 172, 174 are aligned with the projection 136, the stylet 22 advances distally within the lumen 50 defined by the first handle portion 16 due to the force being applied on the projection 136 by the spring 24. Movement of the stylet 22 distally within the lumen 97 of the elongate member 20 applies a distally-directed force on the anchor 28 such that it can be advanced out of the elongate member 20 and introduced at a point of treatment along with a distal portion of the connector 30.

When the projection 136 is disposed between the actuator 26 and the proximal end 40 of the first handle portion 16, the stylet 22 is positioned relative to the handle 32 such that a portion of the stylet 22 and a portion of the handle 32 (e.g., the protuberance 60) define the passageway 69 through which the connector 30 is disposed. As shown in FIG. 3, when the stylet 22 is in the first configuration, the proximal end 130 of the stylet 22 is disposed at the protuberance end 68 and the distal end 132 of the stylet 22 is disposed proximal to the distal end 92 of the elongate member 20. When the stylet 22 is in the first position, the passageway 69 is circumferentially closed and the connector 30 is releasably attached to the first handle portion 16. As the stylet 22 is advanced distally relative to the handle 32, the proximal end 130 of the stylet 22 moves toward the distal end 36 of the handle 32 such that the passageway 69 cooperatively defined by the stylet 22 and the handle 32 circumferentially opens. As shown in FIG. 4, when the stylet 22 is in the second configuration, the proximal end 130 of the stylet 22 is disposed proximal to the protuberance end 68 and the distal end 132 of the stylet 22 is disposed at the distal end 92 of the elongate member 20. When the stylet 22 is in the second position, the passageway 69 is circumferentially open and the connector 30 is free of attachment to, and can be removed from, the handle 32.

Each of the first handle portion 16, second handle portion 18, elongate member 20, stylet 22, spring 24, actuator 26, anchor 28, connector 30, and retention mechanism 14 can be fabricated using any suitable technique or method of manufacture. Skilled artisans will be able to select a suitable technique or method of manufacture to fabricate a first handle portion, second handle portion, elongate member, stylet, spring, actuator, anchor, connector, and/or retention mechanism according to a particular embodiment based on various considerations, including the material(s) that forms each component. Example techniques and methods of manufacture considered suitable to fabricate a first handle portion, second handle portion, elongate member, stylet, spring, actuator, anchor, connector, and/or retention mechanism include extrusion processes, molding processes, insert molding, coiling processes, casting processes, machining processes, stamping processes, and any other technique or method considered suitable for a particular application.

FIGS. 5, 6, and 7 illustrate another anchor deployment system 210. The anchor deployment system 210 is similar to the anchor deployment system 10 illustrated in FIGS. 1, 2, 3, and 4 and described above, except as detailed below. Reference numbers in FIGS. 5, 6, and 7 refer to the same structural element or feature referenced by the same number in FIGS. 1, 2, 3, and 4, offset by 200. Thus, the anchor deployment system 210 comprises an anchor deployment device 212, a retention mechanism 214, an anchor 228, and a connector 230. The anchor deployment device 212 has a first handle portion 216, a second handle portion 218, an elongate member 220, a stylet 222, and an actuator 226.

In the illustrated embodiment, the deployment device 212 omits the inclusion of a spring and includes a slidable actuator 226, as described in more detail herein, and the first handle portion 216 defines a protuberance 260 that does not extend toward the distal end 242 of the first handle portion 216. In addition, alternative to defining first and second passageways, the body 244 of the first handle portion 216 defines a slot 402 that extends from a first end 404 to a second end 406. The first end 404 is disposed between the proximal end 240 and the distal end 242 of the first handle portion 216 and the second end 406 is disposed between the first end 404 and the distal end 242 of the first handle portion 216. The slot 402 has a length 403 that is less than the length of the first handle portion 216.

Alternative to defining threads, the body 244 of the first handle portion 216 defines a recess 408 that extends from an outer surface of the first handle portion 216 and toward an inner surface of the first handle portion 216. The recess 408 is disposed between the distal end 242 of the first handle portion 216 and the slot 402. The recess 408 is sized and configured to receive the first protuberance 410 defined by the second handle portion 218, as described in more detail herein.

In the illustrated embodiment, alternative to defining a first set of threads and a second set of threads, the second handle portion 218 defines a first protuberance 410 and a second protuberance 412. The first protuberance 410 extends from an inner surface that defines the lumen 280 and away from an outer surface of the second handle portion 218. The first protuberance 410 extends from the proximal end 270 of the second handle portion 218 and toward the distal end 272 of the second handle portion 218. However, alternative embodiments can include a protuberance that is disposed between the proximal end and the distal end of a second handle portion. The first protuberance 410 is sized and configured to be received by the recess 408 defined by the first handle portion 216. Alternatively, a first handle portion can define a protuberance that is sized and configured to be received by a recess defined by a second handle portion.

The second protuberance 412 extends from an outer surface of the second handle portion 218 and away from an inner surface of the second handle portion 218. The second protuberance 412 extends from the distal end 272 of the second handle portion 218 and toward the proximal end 270 of the second handle portion 218. However, alternative embodiments can include a protuberance that is disposed between the proximal end and the distal end of the second handle portion. The second protuberance 412 is sized and configured to be received by the recess 414 defined by the elongate member 220.

Alternative to defining threads, the body 302 of the hub 294 of the elongate member 220 defines a recess 414 that extends from an inner surface of the hub 294 that defines lumen 308 and toward an outer surface of the hub 294. The recess 414 is disposed between the proximal end 290 and the distal end 292 of the elongate member 220. The recess 414 is sized and configured to receive the second protuberance 412 defined by the second handle portion 218. Alternatively, a hub can define a protuberance that is sized and configured to be received by a recess defined by a second handle portion.

In the illustrated embodiment, the actuator 226 is attached to the stylet 222. The actuator 226 has a first end 352, a second end 354, and a body 356. The actuator 226 has a length 355 that extends from the first end 352 to the second end 354. The first end 352 is attached to the stylet 222 between the proximal end 330 and the distal end 332 of the stylet 222. The actuator 226 extends from the first end 352, through the slot 402 defined by the first handle portion 216, to the second end 354 that is disposed outside of the lumen 250 defined by the first handle portion 216.

The actuator 226 is moveable between a first position and a second position. In the first position, the actuator 226 is disposed a first distance from the proximal end 234 of the handle 232, as shown in FIG. 6. In the second position, the actuator 226 is disposed a second distance from the proximal end 234 of the handle 232 that is greater than the first distance, as shown in FIG. 7. Thus, the actuator 226 is moveable along the lengthwise axis of the handle 232. Movement of the actuator 226 from its first position to its second position results in movement of the stylet 222 from its first position to its second position such that the passageway 269 cooperatively defined by the handle 232 and the stylet 222 moves from its circumferentially closed configuration to its circumferentially open configuration.

FIGS. 8, 9, 10, 11 and 12 illustrate another anchor deployment system 510. The deployment system 510 is similar to the deployment system 10 illustrated in FIGS. 1, 2, 3, and 4 and described above, except as detailed below. Reference numbers in FIGS. 8, 9, 10, 11, and 12 refer to the same structural element or feature referenced by the same number in FIGS. 1, 2, 3, and 4, offset by 500. Thus, the deployment system 510 comprises an anchor deployment device 512, a retention mechanism 514, an anchor 528, and a connector 530. The anchor deployment device 512 has a first handle portion 516, a second handle portion 518, an elongate member 520, a stylet 522, a spring (not shown), and an actuator 526.

In the illustrated embodiment, the body 544 of the first handle portion 516 omits the inclusion of a first opening (e.g., first opening 46) and defines the protuberance 560 between the proximal end 540 and the distal end 542 of the first handle portion 516. The protuberance 560 defines a first passageway wall that cooperatively defines a passageway 569 with a second passageway wall defined by the actuator 526, as described in more detail herein. The protuberance 560 has a first portion 564 and a second portion 566. The first portion 564 extends from an outer surface of the first handle portion 516 and away from the inner surface of the first handle portion 516. The second portion 566 extends from the first portion 564 and toward the actuator 526 when the actuator 526 is in the first position.

In this embodiment, the actuator 526, a dynamic member, defines a second passageway wall that cooperatively defines the passageway 569 with the protuberance 560, a static member. In use, when the actuator 526 is in the first position the passageway 569 is circumferentially closed such that the connector 530 is releasably attached to the first handle portion 516. When the actuator 526 is in the second position the passageway 569 is circumferentially open such that the connector 530 can be removed from the passageway 569.

In the illustrated embodiment, the stylet 522 has a projection 636 that defines a notch 720 that extends from an outer surface of the projection 636 and toward the lengthwise axis of the stylet 522. The proximal end 630 of the stylet 522 has a first outside diameter 633 and the projection 636 has a second outside diameter 635 and a third outside diameter 721. The second outside diameter 635 of the projection 636 is greater than the first outside diameter 633 of the stylet 522. The third outside diameter 721 is less than the second outside diameter 635.

In the illustrated embodiment, the actuator 526 has an actuator body 656 that defines a top member 658, a first projection 660, and a second projection 662. Each of the first projection 660 and second projection 662 has a first end 668 attached to the top member 658 and a second end 670. The first projection 660 has a length 669 that extends from the first end 668 to the second end 670 of the first projection 660. The second projection 662 has a second length 673 that extends from the first end 668 to the second end 670 of the second projection 662. In the illustrated embodiment, the length 669 of the first projection 660 is greater than the length 673 of the second projection 162.

The first projection 660 is separated from the second projection 662 a distance 671 that is less than the second outside diameter 635 of the projection 636 defined by the stylet 522. This structural arrangement provides a mechanical stop to distal advancement of the stylet 522 within the lumen defined by the first handle portion 516 when the actuator 526 is in the first position. Depending on the structural arrangement of a first handle portion and/or a stylet included in a deployment device, a first projection defined by an actuator can be separated from a second projection defined by the actuator by a distance that is greater than the outside diameter of the projection defined by a stylet.

The actuator body 656 defines a protuberance 672 on the first projection 660 that extends from a surface that is directed toward the lengthwise axis of the second projection 662, away from the first projection 660, and toward the lengthwise axis of the second projection 662. The protuberance 672 is multifaceted and corresponds to the structural arrangement of the notch 720 defined by the projection 636. The protuberance 672 extends from the first projection 636 a distance 675. The distance 675 is less than the difference between the second outside diameter 635 and the third outside diameter 721 of the projection 636. This structural arrangement allows the stylet 522 to advance distally through the lumen 550 defined by the first handle portion 516 when the actuator 526 is in the second position and the notch 720 and the protuberance 672 are aligned.

The position of the first projection 660 within the first handle portion 516 is configured to maintain the position of the stylet 522 when the projection 636 is disposed between the actuator 526 and the proximal end 534 of the handle 532. The distance 675 that the protuberance 672 extends from the first projection 660 is sized and configured to be received by the notch 720 defined by the projection 636 such that the projection 636 can pass through the actuator 526 when the notch 720 and the protuberance 672 are aligned. This structural arrangement provides an actuator 526 that has a first keyed structure and a stylet 522 that has a second keyed structure that corresponds to the first keyed structure such that when the actuator 526 is in the first position the stylet 522 is in the first position and when the actuator 526 is in the second position the stylet 522 can advance to the second position via the force being applied to the projection 636 by the spring.

FIGS. 13, 14, 15, and 16 illustrate another anchor deployment system 810. The anchor deployment system 810 is similar to the anchor deployment system 10 illustrated in FIGS. 1, 2, 3, and 4 and described above, except as detailed below. Reference numbers in FIGS. 13, 14, 15, and 16 refer to the same structural element or feature referenced by the same number in FIGS. 1, 2, 3, and 4, offset by 800. Thus, the anchor deployment system 810 comprises an anchor deployment device 812, a retention mechanism 814, an anchor 828, and a connector 830. The anchor deployment device 812 has a first handle portion 816, a second handle portion 818, an elongate member 820, a stylet 822, a spring 824, and an actuator 826.

In the illustrated embodiment, the second handle portion 818 is releasably attached to the proximal end 840 of the first handle portion 816 and defines a protuberance 860. In addition, the elongate member 820 is releasably attached to the distal end 842 of the first handle portion 816.

In the embodiment illustrated, the body 844 of the first handle portion 816 defines a first opening 846, a first set of threads 862, and a second set of threads 863. The first opening 846 is sized and configured to receive the projection 936 of the stylet 822. The first set of threads 862 is defined on an outer surface of the first handle portion 816 and extends from the proximal end 840 toward the distal end 842 of the first handle portion 816. The first set of threads 862 defines a helical structure that is sized and configured to interact with the helical structure defined by the threads 882 on the second handle portion 818 such that the first and second handle portions 816, 818 can be releasably attached to one another. Alternatively, the threads defined by a handle can be disposed between the proximal end and the distal end of the first handle portion and/or on an inner surface of a handle portion.

The second set of threads 863 is defined on an outer surface of the first handle portion 816 and extends from the distal end 842 toward the proximal end 840 of the first handle portion 816. The second set of threads 863 defines a helical structure that is sized and configured to interact with the helical structure defined by the threads 910 on the elongate member 820 such that the elongate member 820 can be releasably attached to the first handle portions 816. Alternatively, the threads defined by a handle can be disposed between the proximal end and the distal end of the first handle portion and/or on the inner surface of a handle portion.

In the illustrated embodiment, the second handle portion 818 is releasably attached to the first handle portion 816 and has a proximal end 870, a distal end 872, and a body 874 that defines a first opening 876, a second opening 878, a lumen 880, and threads 882. The first opening 876 is defined on the proximal end 870 and the second opening 878 is defined on the distal end 872. The lumen 880 extends from the first opening 876 to the second opening 878. The first opening 876 has a first inside diameter 877 that is sized and configured to receive a portion of the stylet 822. Each of the second opening 878 and lumen 880 has a second inside diameter 879 that is greater than the first inside diameter 877 and that is sized and configured to receive a portion of the first handle portion 816.

The threads 882 are defined on an inner surface of the second handle portion 818 and extend from the distal end 872 toward the proximal end 870 of the second handle portion 818. The threads 882 define a helical structure that is sized and configured to interact with the helical structure defined by the first set of threads 862 defined on the first handle portion 816 such that the second handle portion 818 can be releasably attached to the first handle portion 816. Alternatively, the threads defined by a second handle portion can be disposed between the proximal end and the distal end of the second handle portion and/or on an outer surface of the second handle portion.

The protuberance 860 defined by the second handle portion 818 has a first portion 864 and a second portion 866. The first portion 864 extends from the proximal end 870 of the second handle portion 816 and away from the distal end 872. The second portion 866 extends from the first portion 864, toward the lengthwise axis of the second handle portion 818, and toward the distal end 872 of the second handle portion 818 to a protuberance end 868. In the illustrated embodiment, the protuberance 860 is hook-shaped such that it defines a first passageway wall that cooperatively defines the passageway 869 with a second passageway wall defined by the stylet 822. Alternative embodiments can include a hook-shaped protuberance that does not extend toward the distal end of the first handle portion.

Methods of treatment are described herein. While the methods described herein are shown and described as a series of acts, it is to be understood and appreciated that the methods are not limited by the order of acts described and illustrated, as some acts may in accordance with these methods, be omitted, be repeated, or occur in different orders and/or concurrently with other acts described herein. The methods include methods of treatment using an anchor deployment system. While some steps, optional steps, and/or alternative steps are exemplified by performing a gastropexy, the methods, steps, optional steps, and/or alternative steps described herein can also be used to perform any other suitable treatment, and skilled artisans will be able to select a suitable treatment to perform according to the methods, steps, optional steps, and/or alternative steps described herein according to a particular embodiment based on various considerations, such as the condition intended to be treated.

FIG. 17 is a flowchart representation of a method of treatment 1100 using an anchor deployment system.

A step 1102 comprises insufflating the stomach. Another step 1104 comprises locating a feeding tube insertion site. Another step 1106 comprises defining a gastropexy pattern. Another step 1108 comprises introducing a deployment device having a proximal end and a distal end into a bodily passage such that the distal end of the deployment device is disposed within the stomach. Another step 1110 comprises navigating the distal end of the deployment device to a point of treatment within the stomach. Another step 1112 comprises moving the actuator from the first position to the second position. Another step 1114 comprises removing the connector from the passageway defined by the handle and the dynamic member. Another step 1116 comprises with-drawing the deployment device from the stomach. Another step 1118 comprises applying a proximally-directed force on the connector. Another step 1120 comprises advancing the retention mechanism over the connector until it contacts the abdominal wall. Another step 1122 comprises moving the retention mechanism to the first configuration. Another step 1124 comprises removing the retention mechanism from the connector. Another step 1126 comprises removing the connector.

Step 1102 can be accomplished by introducing a catheter (e.g., nasogastric catheter) into the stomach and introducing air through the catheter and into the stomach until a desired amount of distention has been achieved.

An optional step that can be completed prior to step 1102 comprises locating the medial edge of the liver. This optional step can be completed using any suitable visualization device, such as an ultrasound device.

Step 1104 can be accomplished using any suitable visualization technique, such as fluoroscopy, such that a direct path to the stomach can be located.

Step 1106 can comprise any suitable pattern and will be based on the number of anchors intended to be introduced into the stomach. In method 1100, three anchors are intended to be introduced into the stomach, which results in step 1106 being accomplished by placing three equidistant marks (e.g., using a skin marker) from the feeding tube insertion site located in step 1104 and positioning the marks such that they define a triangular pattern. The pattern can be positioned any suitable distance from the feeding tube insertion site (e.g., between about 2 centimeters and about 3 centimeters from the feeding tube insertion site). However, alternative patterns and number of anchors can be used. For example, alternative patterns can include square patterns, rectangular patterns, and any other pattern considered suitable for a particular embodiment. Example number of anchors considered suitable to use in a gastropexy include one, at least one, two, a plurality, three, four, five, and any other number considered suitable for a particular treatment.

Step 1108 can be accomplished using any suitable anchor deployment device included in an anchor deployment system, and skilled artisans will be able to select a suitable anchor deployment device to use in a method of treatment according to a particular embodiment based on various considerations, including the type of treatment being performed. Example anchor deployment devices considered suitable to use in a method of treatment include the anchor deployment devices described herein, such as anchor deployment device 12, anchor deployment device 212, anchor deployment device 512, anchor deployment device 812, variations thereof, and any other anchor deployment device considered suitable for a particular method of treatment. An example anchor deployment device that can be used to accomplish the methods, steps, alternative steps, and/or optional steps described herein is illustrated and described with respect to FIGS. 1, 2, 3, and 4, and comprises a first handle portion 16, a second handle portion 18, an elongate member 20, a stylet 22, a spring 24, and an actuator 26. The anchor deployment device 12 is moveable between a first configuration and a second configuration, as described herein.

Step 1108 can be accomplished by locating one of the marks placed in step 1106 and applying a force on the anchor deployment device that is directed toward the stomach such that the distal end of the deployment device is introduced into the stomach at, or near, the mark.

Step 1110 can be accomplished by applying a force on the anchor deployment device that is directed toward the stomach until the distal end of the anchor deployment device is disposed within the stomach at a desired location.

An optional step that can be completed subsequent to, or during the completion of step 1110, comprises confirming the position of the distal end of the anchor deployment device. This optional step can be accomplished using any suitable visualization technique. Example visualization techniques considered suitable include x-ray, fluoroscopy, ultrasound, magnetic resonance imaging, and any other visualization technique considered suitable for a particular embodiment.

Depending on the anchor deployment device used to complete the method of treatment 1100, step 1112 can be accomplished as described below. If anchor deployment device 12, anchor deployment device 512, or anchor deployment device 812 is being utilized to complete method 1100, step 1112 can be accomplished by applying a force on the actuator that is directed toward the handle such that the actuator is moved from the first position to the second position. If anchor deployment device 212 is being utilized to complete method 1100, step 1112 can be accomplished by applying a force on the actuator 226 that is directed toward the distal end 236 of the handle 232 while maintaining the position of the handle 232 such that the actuator 226 is moved from the first position to the second position.

When step 1112 has been completed, the anchor has been advanced distally out of the lumen defined by the elongate member such that the anchor is disposed within the stomach. Deployment of the anchor from the lumen defined by the elongate member is completed without the use of a guide wire. In addition, when step 1112 has been completed, the passageway cooperatively defined by the static component (e.g., handle) and the dynamic member (e.g., stylet, actuator) is in the circumferentially open configuration.

Step 1114 can be accomplished by placing a force on the connector that is directed toward the opening in the circumferentially opened passageway until the connector is free of attachment to the handle. If anchor deployment device 12, anchor deployment device 212, or anchor deployment device 812 is being used to complete method 1100, step 1114 can be completed by removing the connector from the circumferentially open passageway cooperatively defined by the handle and the stylet. If anchor deployment device 510 is being used to complete method 1100, step 1114 can be completed by removing the connector from the circumferentially open passageway cooperatively defined by the handle and the actuator.

Step 1116 can be accomplished by applying a force on any suitable portion of the anchor deployment device that is directed away from the stomach such that the anchor deployment device is advanced proximally and is withdrawn from the stomach.

Step 1114 can optionally be completed prior to, concurrently with, or subsequent to, the completion of step 1116.

Step 1118 can be accomplished by applying a proximally-directed force, directed away from the stomach, on any suitable portion of the connector that is disposed outside of the stomach until the anchor contacts the gastric mucosa (e.g., stomach wall) and until the stomach wall contacts the abdominal wall.

Step 1120 can be accomplished by applying a distally-directed force on the retention mechanism such that the retention mechanism travels over the connector and contacts the abdominal wall. Depending on the configuration of the retention mechanism, an optional step that can be completed prior to step 1120 comprises moving the retention mechanism from the first configuration to the second configuration such that it can be advanced over a portion of the length of the connector. This can be accomplished, for example, by applying a compressive force on the top member and the bottom member of the retention mechanism such that they are advanced toward one another.

Step 1122 can be accomplished, for example, by releasing the compressive force being applied on the top and bottom members of the retention mechanism such that it moves from its second configuration in which it is free to move along the length of the connector to the first configuration in which the retention mechanism is releasably attached to the connector.

An optional step comprises determining if an appropriate amount of tension exists on the connector. This optional step can be accomplished using any suitable visualization technique, such as those described herein, to determine the position of the stomach relative to the abdominal wall. Another optional step comprises moving the retention mechanism from the first configuration to the second configuration such that the anchor can be tightened against the stomach wall. Another optional step comprises applying a proximally-directed force on the connector. This optional step can be accomplished by applying a proximally-directed force, directed away from the stomach, on any suitable portion of the connector that is disposed outside of the stomach until the stomach wall contacts the abdominal wall or until a desired amount of contact between the stomach wall and the abdominal wall has been achieved. Another optional step comprises moving the retention mechanism from the second configuration to the first configuration.

Depending on the number of anchors being used, the following steps may be repeated any suitable number of times: step 1108, step 1110, step 1112, step 1114, step 1116, step 1118, step 1120, 1122, 1124, and/or step 1126. Each of these steps may be completed using the same deployment device used to complete method 1100, or a different deployment device can be used. If the same deployment device is used, another optional step comprises attaching a connector to an anchor. Another optional step comprises attaching a retention mechanism to the connector. Another optional step comprises loading the anchor into the deployment device. Another optional step comprises positioning the connector within the passageway cooperatively defined by the static component (e.g., handle) and the dynamic member (e.g., stylet, actuator).

Step 1124 can be accomplished by moving the retention mechanism from the first configuration to the second configuration and by applying a proximally-directed force on the retention mechanism such that it is advanced over the connector and the connector becomes free of the retention mechanism.

Step 1126 can be accomplished by removing the connector using any suitable medical device, such as scissors. Alternatively, if a connector is formed of a bioabsorbable material, step 1126 can be omitted from method 1100. Optionally, step 1126 can be completed prior to step 1124.

An optional step that can be completed subsequent to all of the anchors being positioned within the stomach comprises making an incision at the feeding tube insertion site. Another optional step comprises inserting a feeding tube through the incision. Another optional step comprises removing the feeding tube. Another optional step comprises closing the incision.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. An anchor deployment system comprising:
   a handle having a handle body defining a first passageway wall;
   an elongate member releasably attached to the handle and having an elongate member body defining an elongate member lumen;
   a dynamic member partially disposed within the handle, the dynamic member moveable relative to the handle between a first position and a second position and having a dynamic member body defining a second passageway wall that cooperatively defines a passageway with the first passageway wall, the passageway circumferentially closed when the dynamic member is in the first position and circumferentially open when the dynamic member is in the second position;
   an anchor disposed within the elongate member lumen;
   a connector having a first end, a second end, and a length extending from the first end to the second end, the first end attached to the anchor, the connector extending from the first end through the passageway such that the connector is releasably attached to the handle when the dynamic member is in the first position and is free of attachment to the handle when the dynamic member is in the second position; and
   a retention mechanism disposed along the length of the connector, the retention mechanism moveable between a first configuration in which the retention mechanism is releasably attached to the connector and a second configuration in which the retention mechanism is free of attachment to the connector.

2. The deployment system of claim 1, wherein the dynamic member comprises a stylet partially disposed within the elongate member lumen.

3. The deployment system of claim 2, further comprising an actuator partially disposed within the handle, the actuator moveable between a first position and a second position such that when the actuator is in the first position the stylet is in the first position and when the actuator is in the second position the stylet is in the second position.

4. The deployment system of claim 1, further comprising a stylet partially disposed within the handle and the elongate member lumen, the stylet moveable between a first position and a second position; and
   wherein the dynamic member comprises an actuator;
   wherein the stylet is in the first position when the actuator is in the first position; and
   wherein the stylet is in the second position when the actuator is in the second position.

5. The deployment system of claim 4, wherein the handle has a proximal end and a distal end and the handle body defines a handle lumen;
   wherein the actuator is partially disposed within the handle lumen and comprises an actuator body that defines a first keyed structure; and
   wherein the stylet has a projection that has a second keyed structure that corresponds to the first keyed structure, the projection disposed within the handle lumen between the actuator and the proximal end of the handle when the actuator is in the first position and between the actuator and the distal end of the handle when the actuator is in the second position.

6. The deployment system of claim 5, further comprising a spring disposed within the handle lumen between the projection and the proximal end of the handle, the spring having a compressed configuration when the actuator is in the first position and an expanded configuration when the actuator is in the second configuration.

7. The deployment system of claim 1, wherein the elongate member body defines a slot that extends from the distal end of the elongate member toward the proximal end, the slot providing access to the elongate member lumen.

8. The deployment system of claim 7, wherein the slot is sized and configured to receive a portion of the connector; and
wherein a portion of the connector is disposed within the slot.

9. An anchor deployment system comprising:
a handle having a handle body defining a first passageway wall;
an elongate member releasably attached to the handle and having an elongate member body defining an elongate member lumen;
a dynamic member partially disposed within the handle, the dynamic member moveable relative to the handle between a first position and a second position and having a dynamic member body defining a second passageway wall that cooperatively defines a passageway with the first passageway wall, the passageway circumferentially closed when the dynamic member is in the first position and circumferentially open when the dynamic member is in the second position;
an anchor disposed within the elongate member lumen;
a connector having a first end, a second end, and a length extending from the first end to the second end, the first end attached to the anchor, the connector extending from the first end through the passageway such that the connector is releasably attached to the handle when the dynamic member is in the first position and is free of attachment to the handle when the dynamic member is in the second position; and
a retention mechanism disposed along the length of the connector, the retention mechanism moveable between a first configuration in which the retention mechanism is releasably attached to the connector and a second configuration in which the retention mechanism is free of attachment to the connector;
wherein the dynamic member comprises a stylet partially disposed within the elongate member lumen;
further comprising an actuator partially disposed within the handle, the actuator moveable between a first position and a second position such that when the actuator is in the first position the stylet is in the first position and when the actuator is in the second position the stylet is in the second position;
wherein the handle has a proximal end and a distal end and the handle body defines a handle lumen;
wherein the actuator is partially disposed within the handle lumen and comprises an actuator body that defines a first keyed structure; and
wherein the stylet has a projection that has a second keyed structure that corresponds to the first keyed structure, the projection disposed within the handle lumen between the actuator and the proximal end of the handle when the actuator is in the first position and between the actuator and the distal end of the handle when the actuator is in the second position.

10. The deployment system of claim 9, further comprising a spring disposed within the handle lumen between the projection and the proximal end of the handle, the spring having a compressed configuration when the actuator is in the first position and an expanded configuration when the actuator is in the second configuration.

11. An anchor deployment system comprising:
a handle having a handle body defining a first passageway wall;
an elongate member releasably attached to the handle and having an elongate member body defining an elongate member lumen and an elongate member length;
a stylet partially disposed within the handle and the elongate member lumen, the stylet moveable relative to the handle between a first position and a second position and having a stylet body and a stylet length, the stylet body defining a second passageway wall that cooperatively defines a passageway with the first passageway wall, the passageway circumferentially closed when the stylet is in the first position and circumferentially open when the stylet is in the second position, the stylet length being greater than the elongate member length;
an actuator partially disposed within the handle and moveable between a first position and a second position such that when the actuator is in the first position the stylet is in the first position and when the actuator is in the second position the stylet is in the second position;
an anchor disposed within the elongate member lumen;
a connector having a first end, a second end, and a length extending from the first end to the second end, the first end attached to the anchor, the connector extending from the first end through the passageway such that the connector is releasably attached to the handle when the stylet is in the first position and is free of attachment to the handle when the stylet is in the second position; and
a retention mechanism disposed along the length of the connector, the retention mechanism moveable between a first configuration in which the retention mechanism is releasably attached to the connector and a second configuration in which the retention mechanism is free of attachment to the connector.

12. An anchor deployment system comprising:
a handle having a handle body defining a first passageway wall;
an elongate member releasably attached to the handle and having an elongate member body defining an elongate member lumen and an elongate member length;
a stylet partially disposed within the handle and the elongate member lumen, the stylet moveable relative to the handle between a first position and a second position and having a stylet body and a stylet length, the stylet body defining a second passageway wall that cooperatively defines a passageway with the first passageway wall, the passageway circumferentially closed when the stylet is in the first position and circumferentially open when the stylet is in the second position, the stylet length being greater than the elongate member length;
an actuator partially disposed within the handle and moveable between a first position and a second position such that when the actuator is in the first position the stylet is in the first position and when the actuator is in the second position the stylet is in the second position;
an anchor disposed within the elongate member lumen;
a connector having a first end, a second end, and a length extending from the first end to the second end, the first end attached to the anchor, the connector extending from the first end through the passageway such that the connector is releasably attached to the handle when the stylet is in the first position and is free of attachment to the handle when the stylet is in the second position; and a retention mechanism disposed along the length of the connector, the retention mechanism moveable between a first configuration in which the retention mechanism is releasably attached to the connector and a second configuration in which the retention mechanism is free of attachment to the connector;

wherein the handle has a proximal end and a distal end and the handle body defines a handle lumen;

wherein the actuator is partially disposed within the handle lumen and comprises an actuator body that defines a first keyed structure; and wherein the stylet has a projection that has a second keyed structure that corresponds to the first keyed structure, the projection disposed within the handle lumen between the actuator and the proximal end of the handle when the actuator is in the first position and between the actuator and the distal end of the handle when the actuator is in the second position.

13. The deployment system of claim 12, further comprising a spring disposed within the handle lumen between the projection and the proximal end of the handle, the spring having a compressed configuration when the actuator is in the first position and an expanded configuration when the actuator is in the second configuration.

14. The deployment system of claim 11, wherein the elongate member body defines a slot that extends from the distal end of the elongate member toward the proximal end, the slot providing access to the elongate member lumen.

15. The deployment system of claim 14, wherein the slot is sized and configured to receive a portion of the connector; and wherein a portion of the connector is disposed within the slot.

* * * * *